(12) United States Patent
Schönbrunn et al.

(10) Patent No.: US 12,187,686 B2
(45) Date of Patent: Jan. 7, 2025

(54) BRD4-JAK2 INHIBITORS

(71) Applicant: H. LEE MOFFITT CANCER CENTER AND RESEARCH INSTITUTE, INC., Tampa, FL (US)

(72) Inventors: Ernst Schönbrunn, Tampa, FL (US); Nicholas J. Lawrence, Tampa, FL (US); Harshani R. Lawrence, Tampa, FL (US); Gary Reuther, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 852 days.

(21) Appl. No.: 17/274,287

(22) PCT Filed: Sep. 9, 2019

(86) PCT No.: PCT/US2019/050147
§ 371 (c)(1),
(2) Date: Mar. 8, 2021

(87) PCT Pub. No.: WO2020/051571
PCT Pub. Date: Mar. 12, 2020

(65) Prior Publication Data
US 2021/0355088 A1    Nov. 18, 2021

Related U.S. Application Data

(60) Provisional application No. 62/728,465, filed on Sep. 7, 2018, provisional application No. 62/728,457, filed on Sep. 7, 2018.

(51) Int. Cl.
C07D 239/47    (2006.01)
C07D 401/12    (2006.01)

(52) U.S. Cl.
CPC ......... *C07D 239/47* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 2009/0286789 A1 * | 11/2009 | Hood | A61K 31/4545 514/235.8 |
| 2011/0212077 A1 * | 9/2011 | Noronha | A61K 31/4545 544/323 |
| 2012/0149687 A1 | 6/2012 | Lee et al. | |
| 2017/0210730 A1 | 7/2017 | Bhide et al. | |
| 2022/0119370 A1 * | 4/2022 | Schönbrunn | A61K 45/06 |

FOREIGN PATENT DOCUMENTS

| | | | | |
|---|---|---|---|---|
| WO | WO-2010017122 A2 * | 2/2010 | | A61K 31/506 |
| WO | WO-2010058030 A1 * | 5/2010 | | C07D 239/47 |
| WO | WO-2017059319 A2 * | 4/2017 | | A61K 31/437 |

OTHER PUBLICATIONS

Rothman et al., "The use of common genetic polymorphisms to enhance the epidemiologic study of environmental carcinogens", 2000, Biochemica et Biohysica Acta, 1471, C1-C10 (Year: 2000).*
Phuangsawai et al., "Evaluation of the anti-malarial activity and cytotoxicity of 2,4-diamino-pyrimidine-based kinase inhibitors", 2016, European Journal of Medicinal Chemistry, 124, pp. 896-905 (Year: 2016).*
Choe et al., "Structure-activity relationship study of 2,4-dianilinopyrimidine containig methanesulfonamide (TRE-069) as potent and selective epidermal growth factor receptor T790M/C797S mutant inhibitor for anticancer treatment", 2017, Bulletin of the Korean Chemical Society, pp. 1353-1357 (Year: 2017).*
International Search Report and Written Opinion in PCT/US2019/050147. Mailed Jan. 9, 2020. 11 pages.
Pubchem, Substance Record for SID 181688675. Jun. 9, 2014. https://pubchem.ncbi.nlm.nih.gov/substance/181688675.

* cited by examiner

*Primary Examiner* — Jeffrey H Murray
*Assistant Examiner* — Madeline E Braun
(74) *Attorney, Agent, or Firm* — Meunier Carlin & Curfman LLC

(57) ABSTRACT

Disclosed herein are compounds that are inhibitors of BDR4 and their use in the treatment of cancer. Methods of screening for selective inhibitors of BDR4 are also disclosed. In certain aspects, disclosed are compounds of Formula I, II, and II.

8 Claims, No Drawings

BRD4-JAK2 INHIBITORS

CROSS REFERENCE TO RELATED APPLICATIONS

This application is a United States National Phase Patent Application of International Patent Application Number PCT/US2019/050147, filed on Sep. 9, 2019, which claims the benefit of priority to U.S. Provisional Application No. 62/728,457, filed Sep. 7, 2018 and U.S. Provisional Application No. 62/728,465, filed Sep. 7, 2018 which are incorporated by reference herein in their entireties.

FIELD

The subject matter disclosed herein relates generally to cancer therapy and to anti-cancer compounds. More specifically, the subject matter disclosed herein relates to inhibitors of BDR4 and their use in the treatment of cancer. Methods of screening for selective inhibitors of BDR4 are also disclosed.

BACKGROUND

Bromodomain (BRD)-containing proteins are essential for the recognition of acetylated lysine (KAc) residues of histones during transcriptional activation (Sanchez et al., The role of human bromodomains in chromatin biology and gene transcription. *Current opinion in drug discovery & development* 2009, 12, 659-65). BRDs have emerged as promising drug targets for a number of disease pathways that are characterized by changes in the epigenetic cell signature (Id.; Filippakopoulos et al., Selective inhibition of BET bromodomains. *Nature* 2010, 468, 1067-731). To date, only a few structurally diverse BRD inhibitors have been reported, all of which specifically target the KAc recognition sites of the bromodomain and extra terminal (BET) family of proteins (BRD2, BRD3, BRD4, and BRDT), each containing two tandem BRDs (Hewings et al., Progress in the development and application of small molecule inhibitors of bromodomain-acetyl-lysine interactions. *J Med Chem* 2012, 55, 9393-413; Muller et al., Bromodomains as therapeutic targets. *Expert Rev Mol Med* 2011, 13, e29; Prinjha et al., Place your BETs: the therapeutic potential of bromodomains. *Trends Pharmacol Sci* 2012, 33, 146-53). BET-inhibitors exert a broad spectrum of desirable biological effects such as anticancer and anti-inflammatory properties (Delmore et al., BET bromodomain inhibition as a therapeutic strategy to target c-Myc. *Cell* 2011, 146, 904-17; Matzuk et al., Small-Molecule Inhibition of BRDT for Male Contraception. *Cell* 2012, 150, 673-684; Mertz et al., Targeting MYC dependence in cancer by inhibiting BET bromodomains. *Proc Nat Acad Sci USA* 2011, 108, 16669-74; Ott et al., BET bromodomain inhibition targets both c-Myc and IL7R in high-risk acute lymphoblastic leukemia. *Blood* 2012, 120, 2843-52; Puissant et al., Targeting MYCN in neuroblastoma by BET bromodomain inhibition. *Cancer Discov* 2013, 3, 308-23). Of these, I-BET-762 (GSK525762) has recently entered clinical trials for the treatment of NUT midline carcinoma (Mirguet et al., Discovery of epigenetic regulator I-BET762: lead optimization to afford a clinical candidate inhibitor of the BET bromodomains. *J Med Chem* 2013, 56, 7501-15). Intense efforts are currently underway to discover new chemical scaffolds for hit-to-lead development campaigns of BET inhibitors as novel therapeutics (Filippakopoulos et al., Benzodiazepines and benzotriazepines as protein interaction inhibitors targeting bromodomains of the BET family. *Bioorg Med Chem* 2012, 20, 1878-86; Fish et al., Identification of a chemical probe for bromo and extra C-terminal bromodomain inhibition through optimization of a fragment-derived hit. *J Med Chem* 2012, 55, 9831-7; Mirguet et al., Naphthyridines as Novel BET Family Bromodomain Inhibitors. *Chem Med Chem* 2014, 9, 580-9; Seal et al., Identification of a novel series of BET family bromodomain inhibitors: binding mode and profile of I-BET151 (GSK1210151A). *Bioorg & Med Chem Lett* 2012, 22, 2968-72). Recently, BETs were discovered that interact with diverse kinase inhibitors (Martin et al., Cyclin-dependent kinase inhibitor dinaciclib interacts with the acetyl-lysine recognition site of bromodomains. *Chem Biol* 2013, 8, 2360; Ember et al., The acetyl-lysine binding site of bromodomain-containing protein 4 (BRD4) interacts with diverse kinase inhibitors. *Chem Biol* 2014; Ciceri et al., Dual kinase-bromodomain inhibitors for rationally designed polypharmacology. *Nat Chem Biol* 2014). Among these, the PLK1 inhibitor BI2536 and the JAK2/FLT3 inhibitors TG101348 and TG101209 inhibited the binding of KAc peptide to BRD4 with $IC_{50}$ values of 0.03 and 0.13 µM, respectively, and showed strong downregulation of c-Myc in MM.1S cells. These activities were similar to that of the prototypic BET inhibitor JQ1, the most potent BRD4 inhibitor described to date. Furthermore, TG101348, but not JAK2 inhibitors that lack BET and FLT3 activity, potently inhibited proliferation of MV4-11 AML cells ($IC_{50}$=79 nM)(Id.). AML is often driven by BETs and mutant FLT38 (Smith et al., Validation of ITD mutations in FLT3 as a therapeutic target in human acute myeloid leukaemia. *Nature* 2012, 485, 260-3) and the findings by Knapp and colleagues provided compelling evidence of an oncology indication that could be exploited through dual targeting of kinases and bromodomains. What are thus needed are new BRD inhibitors, for example, those with dual targeting activity, and uses of such inhibitors to treat various cancers. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of BDRs, e.g., BDR4, and their use in the treatment of cancer. Methods of screening for new BDR inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substitutent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is repressed by the formula —N$_3$.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Disclosed are compounds that are BDR4 inhibitors. These disclosed compounds can be used in various compositions as anti-cancer therapeutics.

In certain embodiments, the disclosed compounds have the chemical structure shown in Formula I.

(I)

wherein
X is selected from CH or N;
$Y^1$, $Y^2$, $Y^3$, and $Y^4$ are independently selected from C, CH, or N;
$Z^1$, $Z^2$, $Z^3$, and $Z^4$ are independently selected from C, CH, or N;
$R^{2a}$ is selected from halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl
$R^{3b}$ and $R^{3c}$ are independently selected from hydrogen and substituted or unsubstituted $C_1$-$C_6$ alkyl;
$L^1$ is selected from a $(CH_2)_nSO_2$;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^{5a}$, $R^{5b}$, $R^{5d}$, and $R^{5e}$ are independently absent or selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from -$L^2Q^2$;
$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^{3c})$, $(CH_2)_nN(R^{3c})SO_2$, $(CH_2)_nN(R^{3c})P(O)(R^{3c})$, and $(CH_2)_nP(O)N(R^{3c})$; $R^{3c}$ is in each case independently selected from hydrogen and substituted or unsubstituted $C_1$-$C_6$ alkyl;

$Q^2$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide);

$R^{6a}$ are independently absent or selected from hydrogen, $C_1$-$C_6$ alkyl, $C_1$-$C_6$ alkoxy, halogen, hydroxy, carboxyl, amino, nitro, cyano, and isocyano or $L^1$ and $R^{6a}$ combine with atoms to which they are attached to form a cyclic or heterocyclic ring; and n in each case is independently selected from 0, 1, 2, 3, 4, 5, 6, 7, 8, 9 and 10; or a salt thereof.

In some embodiments of Formula I, the compound can have a structure represented by Formula (I-A):

(I-A)

wherein
$Y^1$, $Y^2$, $Y^3$, and $Y^4$ are independently selected from C, CH, or N;
$Z^1$, $Z^2$, $Z^3$, and $Z^4$ are independently selected from C, CH, or N;
$R^{2a}$, $R^{3b}$, and $R^{3c}$ are independently selected from hydrogen and substituted or unsubstituted $C_1$-$C_6$ alkyl;
$L^1$ is selected from a $(CH_2)_nSO_2$;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^{5a}$, $R^{5b}$, $R^{5d}$, and $R^{5e}$ are independently absent or selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from -$L^2Q^2$;
$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^{3c})$, $(CH_2)_nN(R^{3c})SO_2$, $(CH_2)_nN(R^{3c})P(O)(R^{3c})$, and $(CH_2)_nP(O)N(R^{3c})$;
$R^{3c}$ is in each case independently selected from hydrogen and substituted or unsubstituted $C_1$-$C_6$ alkyl;
$Q^2$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide);
$R^{6a}$ are independently absent or selected from hydrogen, $C_1$-$C_6$ alkyl, $C_1$-$C_6$ alkoxy, halogen, hydroxy, carboxyl, amino, nitro, cyano, and isocyano or $L^1$ and $R^{6a}$ combine with atoms to which they are attached to form a cyclic or heterocyclic ring; and n in each case is independently selected from 0, 1, 2, 3, 4, 5, 6, 7, 8, 9 and 10;
or a salt thereof.

In some embodiments of Formula I, the compound can have a structure represented by Formula (I-B):

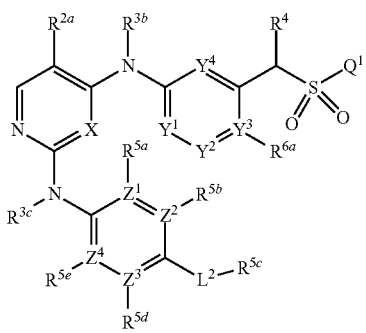

(I-B)

wherein
X is selected from CH, or N;
$Y^1$, $Y^2$, $Y^3$, and $Y^4$ are independently selected from C, CH, or N;
$Z^1$, $Z^2$, $Z^3$, and $Z^4$ are independently selected from C, CH, or N;
$R^{2a}$ is selected from halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;
$R^{3b}$ and $R^{3c}$ are independently selected from hydrogen and substituted or unsubstituted $C_1$-$C_6$ alkyl;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^4$ can be selected from hydrogen, halogen, and substituted or unsubstituted $C_1$-$C_6$ alkyl;
$R^{5a}$, $R^{5b}$, $R^{5d}$, and $R^{5e}$ are independently absent or selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide);
$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^{3c})$, $(CH_2)_nN(R^{3c})SO_2$, $(CH_2)_nN(R^{3c})P(O)(R^{3c})$, and $(CH_2)_nP(O)N(R^{3c})$;
$R^{3c}$ is in each case independently selected from hydrogen and substituted or unsubstituted $C_1$-$C_6$ alkyl;
$R^{6a}$ is absent or selected from hydrogen, $C_1$-$C_6$ alkyl, $C_1$-$C_6$ alkoxy, halogen, hydroxy, carboxyl, amino, nitro, cyano, and isocyano or $R^4$ and $R^{6a}$ combine with atoms to which they are attached to form a cyclic or heterocyclic ring; and
n in each case is independently selected from 0, 1, 2, 3, 4, 5, 6, 7, 8, 9 and 10; or a salt thereof.

In some embodiments of Formula I, the compound can have a structure represented by Formula I-C:

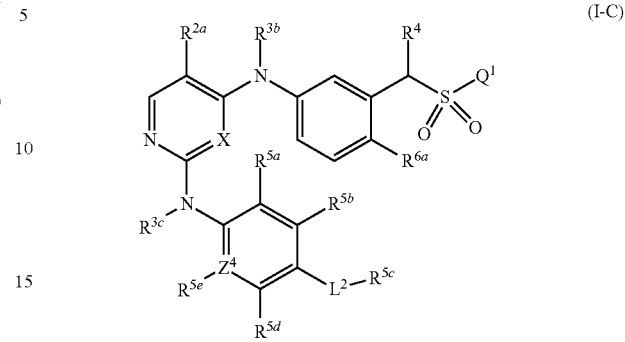

(I-C)

wherein
X is selected from CH, or N;
$Z^4$ is selected from C, CH, or N;
$R^{2a}$ is selected from halogen, $C_1$-$C_6$ alkyl, $C_1$-$C_6$ haloalkyl, cyano, nitro, halogen, amino, substituted or unsubstituted amide, or substituted or unsubstituted $C_2$-$C_5$ heteroaryl;
$R^{3b}$ and $R^{3c}$ are independently selected from hydrogen and substituted or unsubstituted $C_1$-$C_6$ alkyl;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^4$ can be selected from hydrogen, halogen, and substituted or unsubstituted $C_1$-$C_6$ alkyl;
$R^{5a}$, $R^{5b}$, $R^{5d}$, and $R^{5e}$ are independently absent or selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide);
$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^{3c})$, $(CH_2)_nN(R^{3c})SO_2$, $(CH_2)_nN(R^{3c})P(O)(R^{3c})$, and $(CH_2)_nP(O)N(R^{3c})$;
$R^{3c}$ is in each case independently selected from hydrogen and substituted or unsubstituted $C_1$-$C_6$ alkyl;
$R^{6a}$ is absent or selected from hydrogen, $C_1$-$C_6$ alkyl, $C_1$-$C_6$ alkoxy, halogen, hydroxy, carboxyl, amino, nitro, cyano, and isocyano or $R^4$ and $R^{6a}$ combine with atoms to which they are attached to form a cyclic or heterocyclic ring; and
n in each case is independently selected from 0, 1, 2, 3, 4, 5, 6, 7, 8, 9 and 10; or a salt thereof.

In certain embodiments of Formula I, I-A, I-B, and I-C, $Q^1$ is $C_1$-$C_{10}$ alkyl, e.g., methyl, ethyl, n-propyl, isopropyl, n-butyl, isobutyl, tert-butyl, pentyl, or hexyl. In some examples, $Q^1$ can be a $C_2$-$C_6$ alkyl. Preferably, $Q^1$ is a $C_4$ alkyl such as tert-butyl In certain embodiments of Formula I, I-A, I-B, and I-C, $L^1$ is $(CH_2)_nSO_2$; and in some cases n is either 0, 1, or 2. In some examples, n is 1.

In certain embodiments of Formula I, I-A, I-B, and I-C, $R^{2a}$ can be $C_1$-$C_6$ alkyl. For example, $R^{2a}$ can be methyl, ethyl, or propyl. In specific examples, $R^{2a}$ is methyl. In other specific examples, $R^{2a}$ is ethyl. In other examples $R^{2a}$ is $CF_3$. In further embodiments of Formula I, I-A, I-B, and I-C, $R^{2a}$ can be substituted or unsubstituted amide, or substituted or unsubstituted $C_2$-$C_5$ heteroaryl. For example, $R^{2a}$ can be unsubstituted amide. In some examples, $R^{2a}$ is substituted or unsubstituted $C_2$-$C_5$ heteroaryl.

In certain embodiments of Formula I, I-A, I-B, and I-C, $R^{3b}$ and $R^{3c}$ are both hydrogen. In certain instances, $R^{3c}$ is hydrogen and $R^{3b}$ is not hydrogen. In certain instances, $R^{3c}$ is not hydrogen and $R^{3b}$ is hydrogen.

In certain embodiments of Formula I, I-A, I-B, and I-C, $R^4$ can be selected from hydrogen and substituted or unsubstituted $C_1$-$C_6$ alkyl; or $R^4$ and $R^{6a}$ combine with the intervening atoms to which they are attached to form a substituted or unsubstituted cyclic or heterocyclic ring. In certain embodiments of Formula I, I-A, I-B, and I-C, $R^4$ can be selected from hydrogen, halogen. For example, $R^4$ can be halogen, e.g., fluoro, chloro, or bromo. In some examples, $R^4$ can be hydrogen. In certain embodiments of Formula I, I-A, I-B, and I-C, $R^4$ and $R^{6a}$ combine with intervening atoms to which they are attached to form a substituted or unsubstituted cycloalkyl ring.

In certain embodiments of Formula I, I-A, I-B, and I-C, $R^{5a}$ and $R^{5e}$ are both hydrogen. In other examples, $R^{5a}$ and $R^{5d}$ and $R^{5e}$ are all hydrogen. In other examples, $R^{5b}$ and $R^{5e}$ halogen, e.g., fluoro or chloro. In other examples, $R^{5a}$ is halogen, e.g., fluoro or chloro. In other examples, $R^{5d}$ is halogen, e.g., fluoro or chloro. In other examples, $R^{5d}$ is halogen, e.g., fluoro or chloro. In other examples, $R^{5b}$ and $R^{5d}$ are hydrogen or halogen. In certain preferred embodiments, $R^{5a}$, $R^{5e}$, $R^{3a}$ and $R^{3b}$ are each hydrogen. In certain preferred embodiments, $R^{5b}$ and $R^{5d}$ are both hydrogen. In other examples, at least one of $R^{5b}$ and $R^{5d}$ are halogen. For example, $R^{5b}$ and $R^{5d}$ can both be halogen, preferably fluoro. In some embodiments, at least one of $R^{5b}$ and $R^{5d}$ are methyl. In further examples of Formula I, I-A, I-B, and I-C, at least one of $R^4$, $R^{5a}$, $R^{5b}$, $R^{5c}$, $R^{5d}$, and $R^{5e}$ are halogen. In further examples of Formula I, I-A, I-B, and I-C, $R^{5b}$ can be a halogen such as fluoro, chloro, or bromo, preferably fluoro. In some examples, wherein $R^{5a}$, $R^{5e}$, $R^{3a}$ and $R^{3b}$ are each hydrogen. In some examples, at least one of $R^{6a}$, $R^{5a}$, $R^{5b}$, $R^{5c}$, $R^{5d}$, and $R^{5e}$ are halogen. In some examples, $R^{5b}$ and $R^{5d}$ are independently selected from hydrogen or halogen. In some examples, one or both of $R^{5b}$ and $R^{5d}$ are fluoro.

In some instance the compound of Formula I, I-A, or I-B or I-C is characterized, wherein $R^{5c} Q^2$ can be substituted or unsubstituted $C_5$-$C_8$ cycloheteroalkyl, substituted or unsubstituted heteroaryl, substituted or unsubstituted $C_1$-$C_6$ heteroalkyl, or substituted or unsubstituted $C_1$-$C_6$ amide. For example, $R^{5c} Q^2$ can be substituted or unsubstituted $C_5$-$C_8$ cycloheteroalkyl or a substituted or unsubstituted $C_3$-$C_8$ cycloalkyl. In specific examples the $C_5$-$C_8$ cycloheteroalkyl or $C_3$-$C_8$ cycloalkyl can be substituted with $C_1$-$C_8$ alkyl, $C_1$-$C_8$ alkylamine, $C_1$-$C_8$ alkoxy, or substituted heterocycle. Exemplary $C_5$-$C_5$ cycloheteroalkyl and $C_3$-$C_8$ cycloalkyl include

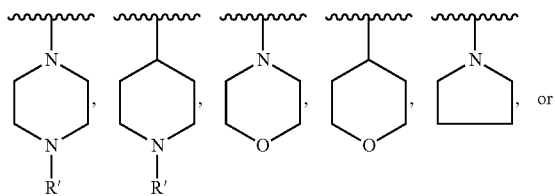

wherein R' is hydrogen, substituted or unsubstituted $C_1$-$C_8$ alkyl, substituted or unsubstituted $C_1$-$C^8$ alkylamine, substituted or unsubstituted $C_1$-$C_8$ alkoxyl, substituted or unsubstituted alkylheterocyle, or substituted or unsubstituted heterocyle.

As described herein, $L^2$ is a linker. In certain embodiments of Formula I, I-A, I-B, and I-C, $L^2$ can be a bond. In other embodiments of Formula I, I-A, I-B, and I-C, $L^2$ can be selected from substituted or unsubstituted $C_1$-$C_6$ heteroalkyl, or substituted or unsubstituted $C_1$-$C_6$ amide. For example, $L^2$ can be an unsubstituted $C_1$-$C_6$ heteroalkyl comprising a heteroatom selected from O, N, or S, or an unsubstituted $C_1$-$C_6$ amide. In some embodiments, $L^2$ can be selected from $(CH_2)_n$, $(CH_2)_nC(O)N(R^{3c})$, $(CH_2)_nN(R^{3c})C(O)$, $(CH_2)_nN(R^{3c})$, $(CH_2)_nC(O)$, and $(CH_2)_nN(R^{3c})C(O)$; n is 0 or 1; and $R^{3c}$ is hydrogen. In some embodiments, $L^2$ is a bond, e.g., wherein $L^2$ is $(CH_2)_n$, and n is 0.

In certain embodiments of Formula I, I-A, I-B, and I-C, $R^{6a}$ can be selected from hydrogen, halogen, or $R^4$ (or $L^1$) and $R^6$ combine with atoms to which they are attached to form a cycloalkenyl ring or a cycloheteroalkenyl ring. For example, $R^{6a}$ can be halogen, e.g., fluoro, chloro, or bromo. In some examples, $R^{6a}$ can be hydrogen. In other examples, $R R^4$ (or $L^1$) and $R^{6a}$ can combine with atoms to which they are attached to form a $C_5$-$C_6$ cycloalkyl ring. In some examples, $R^{6a}$ is absent.

In certain embodiments of Formula I, I-A, I-B, and I-C, X is CH. In other embodiments of Formula I, I-A, I-B, and I-C, X is N.

In certain embodiments of Formula I, I-A, I-B, and I-C, $Y^1$ is CH. In other embodiments of Formula I, I-A, I-B, and I-C, and I-C, $Y^1$ is N. In certain embodiments of Formula I, I-A, I-B, and I-C, $Y^2$ is CH. In other embodiments of Formula I, I-A, I-B, and I-C, and I-C, $Y^2$ is N. In certain embodiments of Formula I, I-A, I-B, and I-C, $Y^3$ is CH. In other embodiments of Formula I, I-A, I-B, and I-C, $Y^3$ is N. In certain embodiments of Formula I, I-A, I-B, and I-C, $Y^4$ is CH. In other embodiments of Formula I, I-A, I-B, and I-C, $Y^4$ is N.

In certain embodiments of Formula I, I-A, I-B, and I-C, $Y^3$ and $Y^4$ are both C. In certain embodiments of Formula I, I-A, I-B, and I-C, at least one of $Y^3$ and $Y^4$ are N. In certain embodiments of Formula I, I-A, I-B, and I-C, at least one of $Y^1$, $Y^2$, $Y^3$, and $Y^4$ are N. In certain embodiments of Formula I, I-A, I-B, and I-C, $Y^1$, $Y^2$, $Y^3$, and $Y^4$ are all C or CH. In some examples, $Y^3$ and $Y^4$ are both C. In some examples, at least one of $Y^3$ and $Y^4$ are N. In some examples, at least one of $Y^1$, $Y^2$, $Y^3$, and $Y^4$ are N. In some examples, $Y^1$, $Y^2$, $Y^3$, and $Y^4$ are all C or CH.

In certain embodiments of Formula I, I-A, I-B, and I-C, $Z^1$ is CH. In other embodiments of Formula I, I-A, I-B, and I-C, $Z^1$ is N. In certain embodiments of Formula I, I-A, I-B, and I-C, $Z^2$ is CH. In other embodiments of Formula I, I-A, I-B, and I-C, $Z^2$ is N. In certain embodiments of Formula I, I-A, I-B, and I-C, $Z^3$ is CH. In other embodiments of Formula I, I-A, I-B, and I-C, $Z^3$ is N. In certain embodiments of Formula I, I-A, I-B, and I-C, $Z^4$ is CH. In other embodiments of Formula I, I-A, I-B, and I-C, $Z^4$ is N.

In certain embodiments of Formula I, I-A, I-B, and I-C, $Z^1$ and $Z^4$ are both C. In certain embodiments of Formula I, I-A, I-B, and I-C, at least one of $Z^1$ and $Z^4$ are N. In certain embodiments of Formula I, I-A, I-B, and I-C, at least one of $Z^1$, $Z^2$, $Z^3$, and $Z^4$ are N. In certain embodiments of Formula I, I-A, I-B, and I-C, $Z^1$, $Z^2$, $Z^3$, and $Z^4$ are all C or CH. In some examples, $Z^1$ and $Y^4$ are both N. In some examples, at least one of $Z^1$ and $Z^4$ are N. In some examples, at least one of $Z^1$, $Z^2$, $Z^3$, and $Z^4$ are N. In some examples, $Z^1$, $Z^2$, $Z^3$, and $Z^4$ are all C or CH.

In certain embodiments, the disclosed compounds have the chemical structure shown in Formula II.

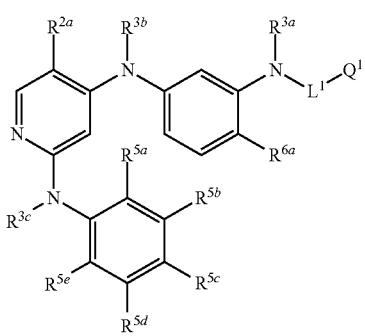

(II)

wherein
$R^{2a}$, $R^{3a}$, $R^{3b}$, and $R^{3c}$ are independently selected from hydrogen and substituted or unsubstituted $C_1$-$C_6$ alkyl;
$L^1$ is selected from a $SO_2$ and $(CH_2)_n SO_2$;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^{5a}$, $R^{5b}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from substituted or unsubstituted cycloalkyl, substituted or unsubstituted heteroaryl, and substituted or unsubstituted heterocycloalkyl;
$R^{6a}$ are independently selected from hydrogen, $C_1$-$C_6$ alkyl, $C_1$-$C_6$ alkoxy, halogen, hydroxy, carboxyl, amino, nitro, cyano, and isocyano; and
n in each case is independently selected from 0, 1, 2, 3, 4, 5, 6, 7, 8, 9 and 10; or a salt thereof.

In certain embodiments of Formula (I or II), $Q^1$ is selected from a substituted or unsubstituted alkyl. In some examples, $Q^1$ is selected from methyl, ethyl, propyl, isopropyl, butyl, isobutyl, and tertbutyl.

In certain embodiments of Formula (I or II), $L^1$ is $SO_2$. In some examples, n is 0 or 1.

In certain embodiments of Formula (I or II), $R^{2a}$ is selected from a unsubstituted $C_1$-$C_6$ alkyl. In some examples, $R^{2a}$ is methyl or ethyl.

In certain embodiments of Formula (I or II), $R^{3a}$, $R^{3b}$, and $R^{3c}$ are all hydrogen.

In certain embodiments of Formula (I or II), wherein $R^{5a}$ and $R^{5e}$ are both hydrogen.

In certain embodiments of Formula (I or II), $R^{5b}$ and $R^{5d}$ are independently selected from hydrogen or halogen. In some examples, one or both of $R^{5b}$ and $R^{5d}$ are fluoro. For example, $R^{5b}$ alone can be fluoro.

In certain embodiments of Formula (I or II), $R^{5c}$ is selected from a substituted or unsubstituted heterocyclyl. In some examples, $R^{5c}$ is selected from:

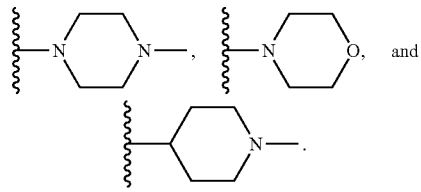

In certain embodiments of Formula (I or II), $R^{6a}$ is selected from a halogen and hydrogen. In some examples, $R^{6a}$ is chloro.

In certain embodiments, the disclosed compounds have the chemical structure shown in Formula III.

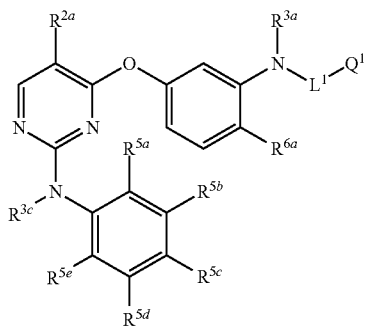

(III)

wherein
$R^{2a}$, $R^{3a}$, and $R^{3c}$ are independently selected from hydrogen and substituted or unsubstituted $C_1$-$C_6$ alkyl;
$L^1$ is selected from a $SO_2$ and $(CH_2)_n SO_2$;
$Q^1$ is selected from substituted or unsubstituted alkyl, substituted or unsubstituted aryl, substituted or unsubstituted cycloalkyl, substituted or unsubstituted heteroaryl, and substituted or unsubstituted heterocycloalkyl;
$R^{5a}$, $R^{5b}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano;
$R^{5c}$ is selected from substituted or unsubstituted cycloalkyl, substituted or unsubstituted heteroaryl, and substituted or unsubstituted heterocycloalkyl;
$R^{6a}$ are independently selected from hydrogen, $C_1$-$C_6$ alkyl, $C_1$-$C_6$ alkoxy, halogen, hydroxy, carboxyl, amino, nitro, cyano, and isocyano; and
n in each case is independently selected from 0, 1, 2, 3, 4, 5, 6, 7, 8, 9 and 10;
or a salt thereof.

In certain embodiments of Formula (I, II, or III), $Q^1$ is selected from a substituted or unsubstituted alkyl. In some examples, $Q^1$ is selected from methyl, ethyl, propyl, isopropyl, butyl, isobutyl, and tertbutyl.

In certain embodiments of Formula (I, II, or III), $L^1$ is $SO_2$. In some examples, n is 0 or 1.

In certain embodiments of Formula (I, II, or III), $R^{2a}$ is selected from a unsubstituted $C_1$-$C_6$ alkyl. In some examples, $R^{2a}$ is methyl or ethyl.

In certain embodiments of Formula (I, II, or III), $R^{3a}$, $R^{3b}$, and $R^{3c}$ are all hydrogen.

In certain embodiments of Formula (I, II, or III), wherein $R^{5a}$ and $R^{5e}$ are both hydrogen.

In certain embodiments of Formula (I, II, or III), $R^{5b}$ and $R^{5d}$ are independently selected from hydrogen or halogen. In some examples, one or both of $R^{5b}$ and $R^{5d}$ are fluoro. For example, $R^{5b}$ alone can be fluoro.

In certain embodiments of Formula (I, II, or III), $R^{5c}$ is selected from a substituted or unsubstituted heterocyclyl. In some examples, $R^{5c}$ is selected from:

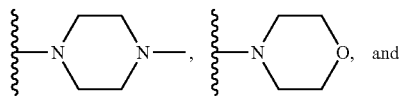, and

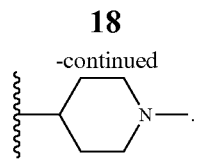

In certain embodiments of Formula (I, II, or III), $R^{6a}$ is selected from a halogen and hydrogen. In some examples, $R^{6a}$ is chloro.

Specific examples of compounds disclosed herein are in table 1.

TABLE 1

| Name<br>Molecular Wt (Amt. Supplied mg) | Co-crystal | DSF ΔTm (° C.) | Estimated BRD4-1 IC$_{50}$ (μM) | Comments |
|---|---|---|---|---|
| | | 8.4 | 5610 nM (BRD4)<br>9 nM (JAK2) | MM1.S cells (sensitive for BRD4 inhibition)<br>EC50: 0.71 μM<br>GI50: 0.44 μM (UKE1 cells) |
| | | 6.9 | | MM1.S cells<br>IC50: 0.13 μM |
| | | 9.2 | 704 nM (BRD4)<br>0.87 nm (JAK2) | GI50: 0.21 μM (UKE1 cells)<br>Mouse microsome 28%<br>MM1.S cells<br>IC50: 0.14 μM |

TABLE 1-continued

| Name Molecular Wt (Amt. Supplied mg) | Co-crystal | DSF ΔTm (° C.) | Estimated BRD4-1 IC$_{50}$ (μM) | Comments |
|---|---|---|---|---|
| [structure: 5-methylpyrimidine with NH linkers to (3-((tert-butylsulfonyl)methyl)-4-chlorophenyl) and (3-fluoro-4-(1-methylpiperidin-4-yl)phenyl)] | | 9.8 | | GI50: 0.40 μM, (UKE1 cells) Mouse microsome 22% MM1.S cells IC50: 0.32 μM |

DSF = Differential Scanning stability of Fluorimetry; provides a measure of the increased stability of BRD4 upon ligand binding
The DSF experiment was run at 100 μM protein, 4 μM compound and 2% DMSO.

Other Specific examples of compounds disclosed herein are in table 2.

TABLE 2

| Name Molecular Wt (Amt. Supplied mg) | Co-crystal | DSF ΔTm (° C.) | Comments |
|---|---|---|---|
| [structure: 5-methylpyridine with NH linkers to (2-chloro-5-((tert-butylsulfonyl)amino)phenyl) and (3-fluoro-4-(4-methylpiperazin-1-yl)phenyl)] | | 6.9 | MM1.S cells (sensitive for BRD4 inhibition) EC50: 3.12 μM GI50: 4.5 μM (UKE1 cells) |
| [structure: similar pyridine compound with 3,5-difluoro-4-(4-methylpiperazin-1-yl)phenyl group] •2 Formic acid | Yes | 6.6 | MM1.S cells (sensitive for BRD4 inhibition) EC50: 2.83 μM GI50: 5.7 μM (UKE1 cells) |

TABLE 2-continued
| Name Molecular Wt (Amt. Supplied mg) | Co-crystal | DSF ΔTm (° C.) | Comments |
|---|---|---|---|
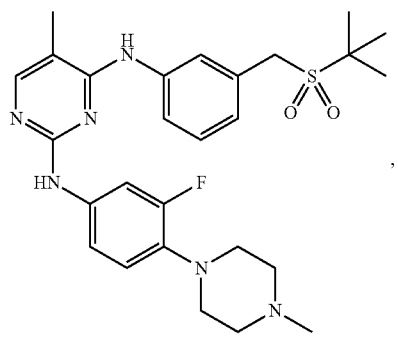
Other specific examples of compounds disclosed herein have a structure
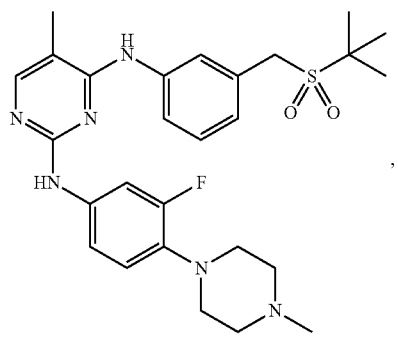
,
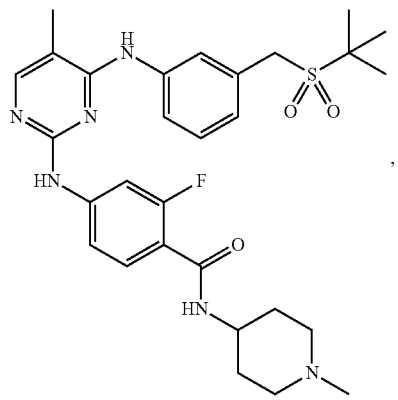
,
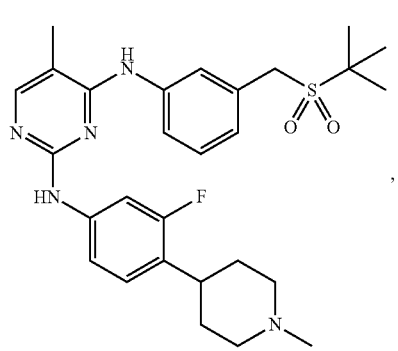
,
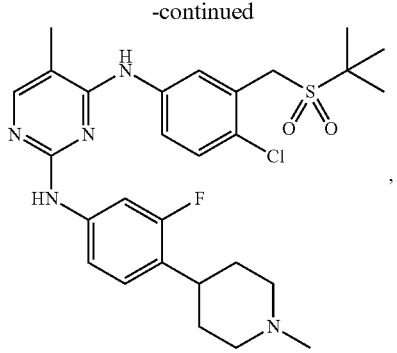
,
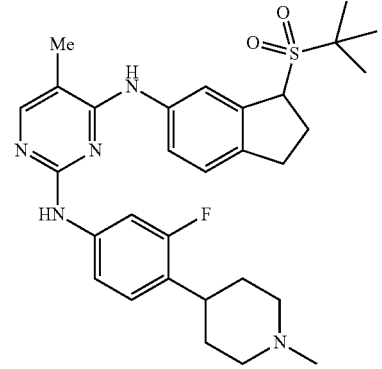
,
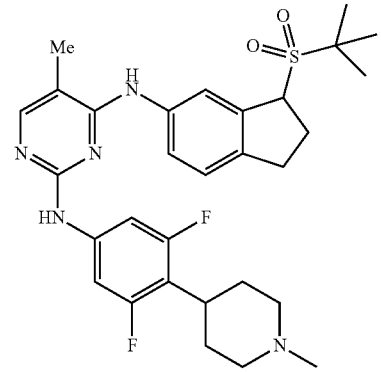
, -continued

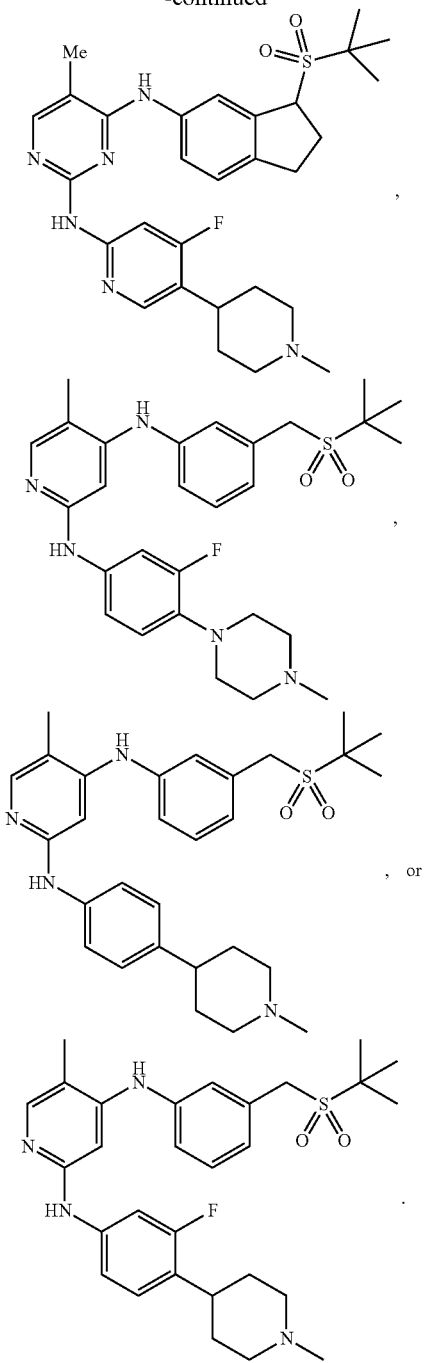

DSF=Differential Scanning Fluorimetry; provides a measure of the increased stability of BRD4 upon ligand binding The DSF experiment was run at 100 μM protein, 4 μM compound and 2% DMSO.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting BDR4 with a target compound and determining whether the compound binds the BDR4, wherein the compound that binds BDR4 is identified as a putative anti-cancer compound.

Examples

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

First, a set of 2-chloro-4-anilinopyrimidines 2 is be prepared by reaction of the 5-substituted dichloropyrimidine 1 ($R^4$=Me, Et, $CF_3$, Cl, F, Br, CN, CCH) with appropriate aniline bearing $R^1$ and $R^2$ groups. Reaction of building blocks 2 with a set of anilines bearing the $R^3$ group will provide the target set of dianilinopyrimidines 3. This modular two-step synthesis will provide rapid access to libraries for analysis of both BRD4 and kinase inhibitory properties.

Cellular activity of promising compounds is assessed using MM.1S and MV4-11 AML cells using c-Myc levels as biomarker (6-12 hr treatment) and antiproliferative activity (48-72 hr treatment) as described (Ciceri et al., Dual kinase-bromodomain inhibitors for rationally designed polypharmacology. *Nat Chem Biol* 2014). The most potent BRD4 inhibitors are profiled against representative panels of kinases and BRDs to assess potency and specificity using commercial services.

The dianilinopyrimidines can be prepared according to Scheme 1, using methods previously reported,[1,2] by reaction of a substituted 2,4-dichloropyrimidine 1 with A-ring aniline 2 to form the 4-anilino-pyrimidine intermediate 3. This intermediate 3, upon reaction with a second set of B-ring anilines 4 under more forcing conditions, generated the final dianilinopyrimidine library 5. Alternatively the reaction of the 4-anilino-pyrimidine intermediate 3 and the B-ring aniline may be effected by palladium catalysis. An alternative approach to certain sulfonamide substituted B-rings involves sulfonylation of dianilinopyrimidine (Scheme 1B).

The synthetic routes to the A-ring anilines bearing a sulfonamide group are shown in Schemes 4A-D. Those shown in Scheme 4A were prepared by reaction of nitrophenylsulfonyl chlorides and amines, followed by reduction of the nitro group.[11] A similar approach is shown for those B-ring anilines prepared from nitroaniline or mono-BOC diaminobenzene derivatives as shown in Scheme 4B.[12]

The B-ring anilines were synthesized according to the routes shown in Schemes 5.[15-17]

Scheme 1

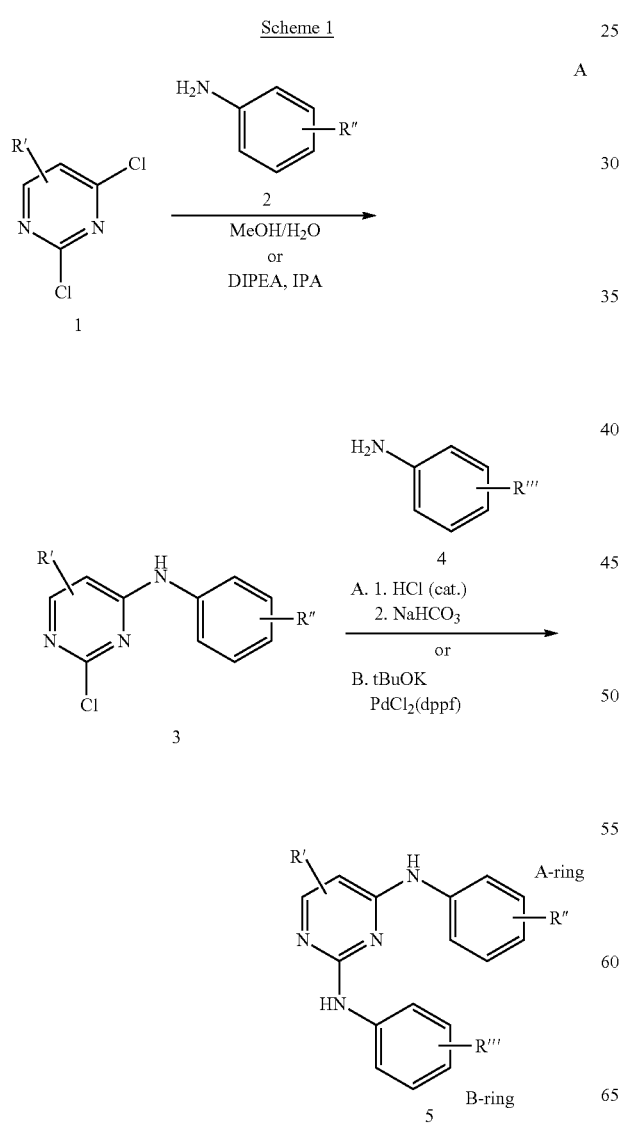

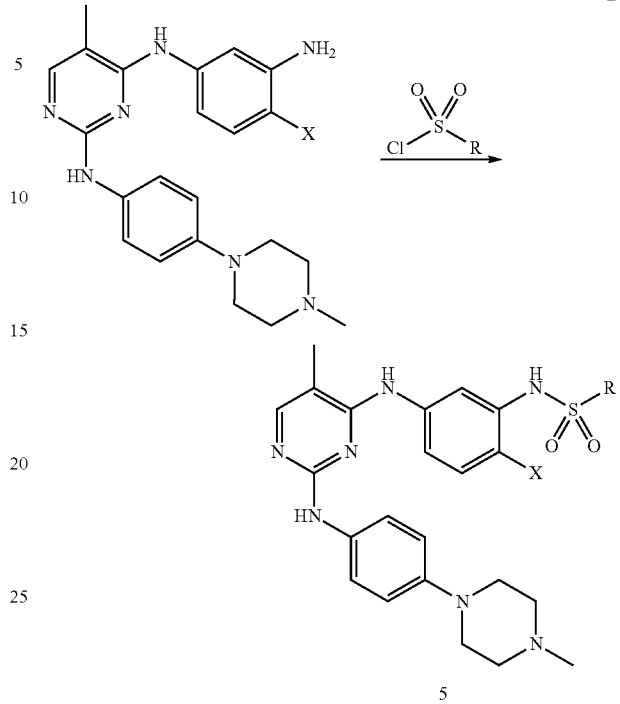

Scheme 4 Synthesis of A-ring anilines with sulfonamides

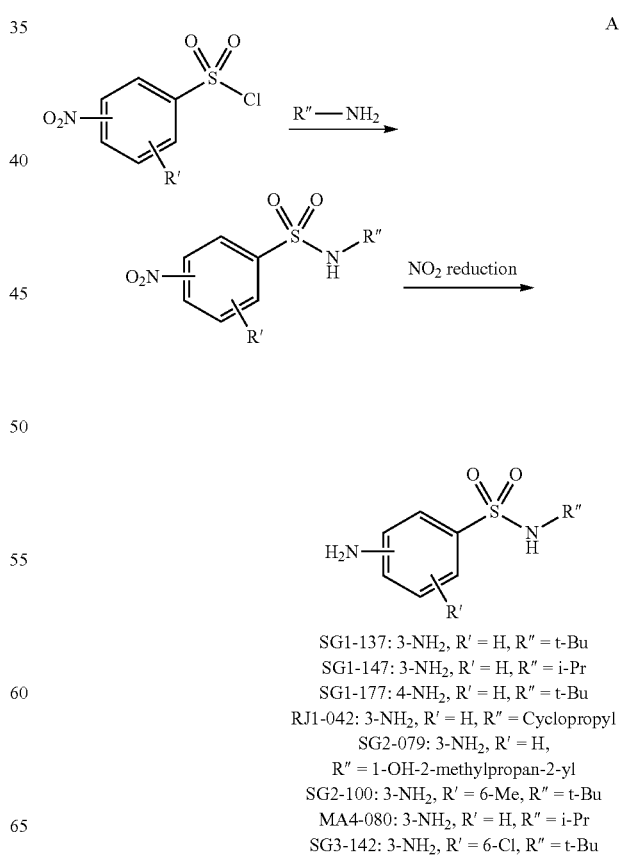

SG1-137: 3-NH₂, R' = H, R" = t-Bu
SG1-147: 3-NH₂, R' = H, R" = i-Pr
SG1-177: 4-NH₂, R' = H, R" = t-Bu
RJ1-042: 3-NH₂, R' = H, R" = Cyclopropyl
SG2-079: 3-NH₂, R' = H,
  R" = 1-OH-2-methylpropan-2-yl
SG2-100: 3-NH₂, R' = 6-Me, R" = t-Bu
MA4-080: 3-NH₂, R' = H, R" = i-Pr
SG3-142: 3-NH₂, R' = 6-Cl, R" = t-Bu

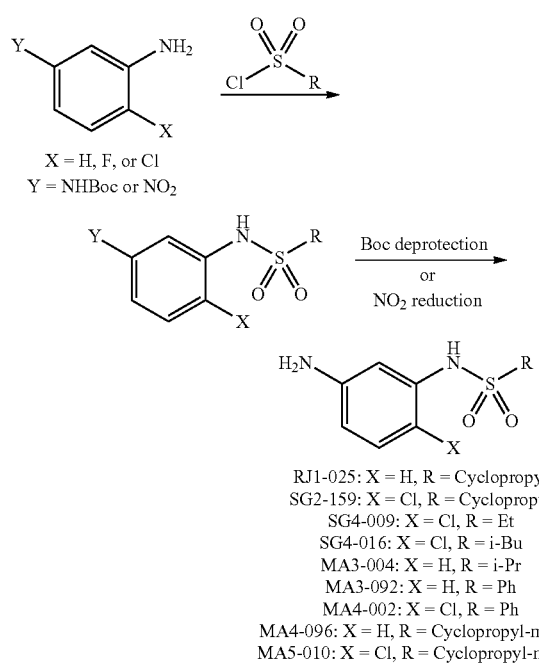
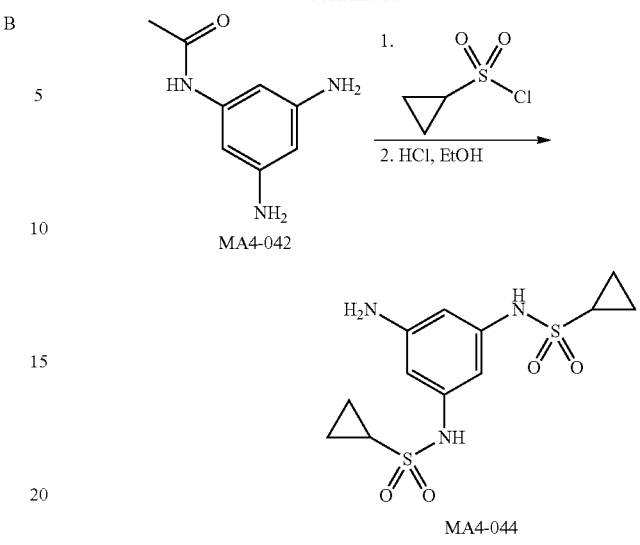
MA4-042
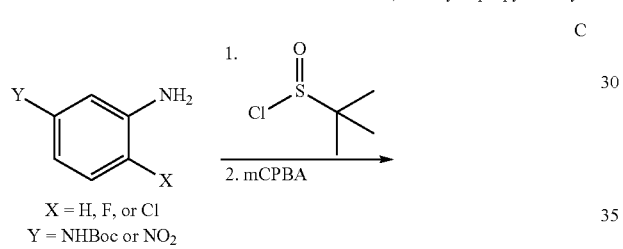
Scheme 5 Synthesis of the B-ring anilines 4
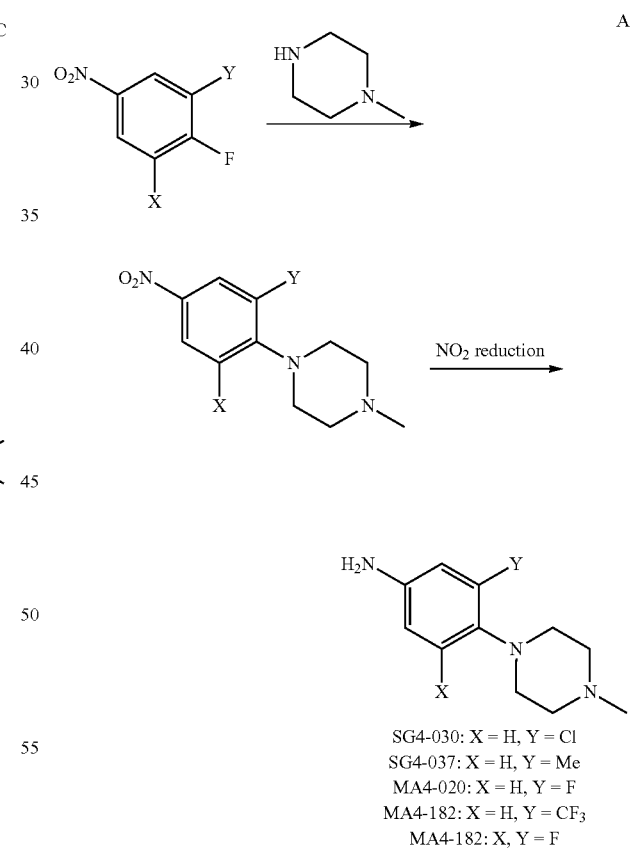
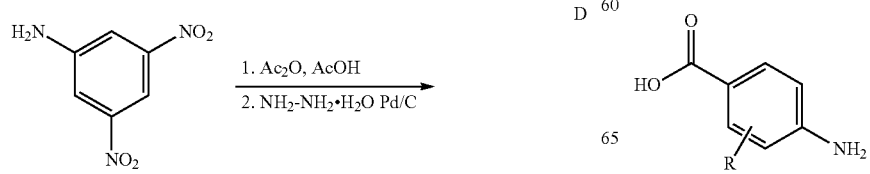
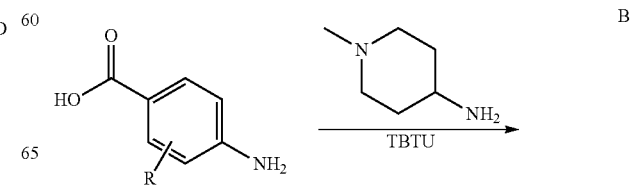

-continued
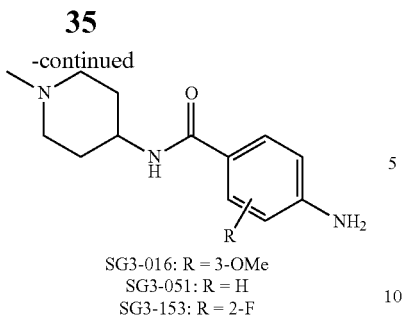
SG3-016: R = 3-OMe
SG3-051: R = H
SG3-153: R = 2-F
Methods for the Synthesis of Sulfonyl Derivatives
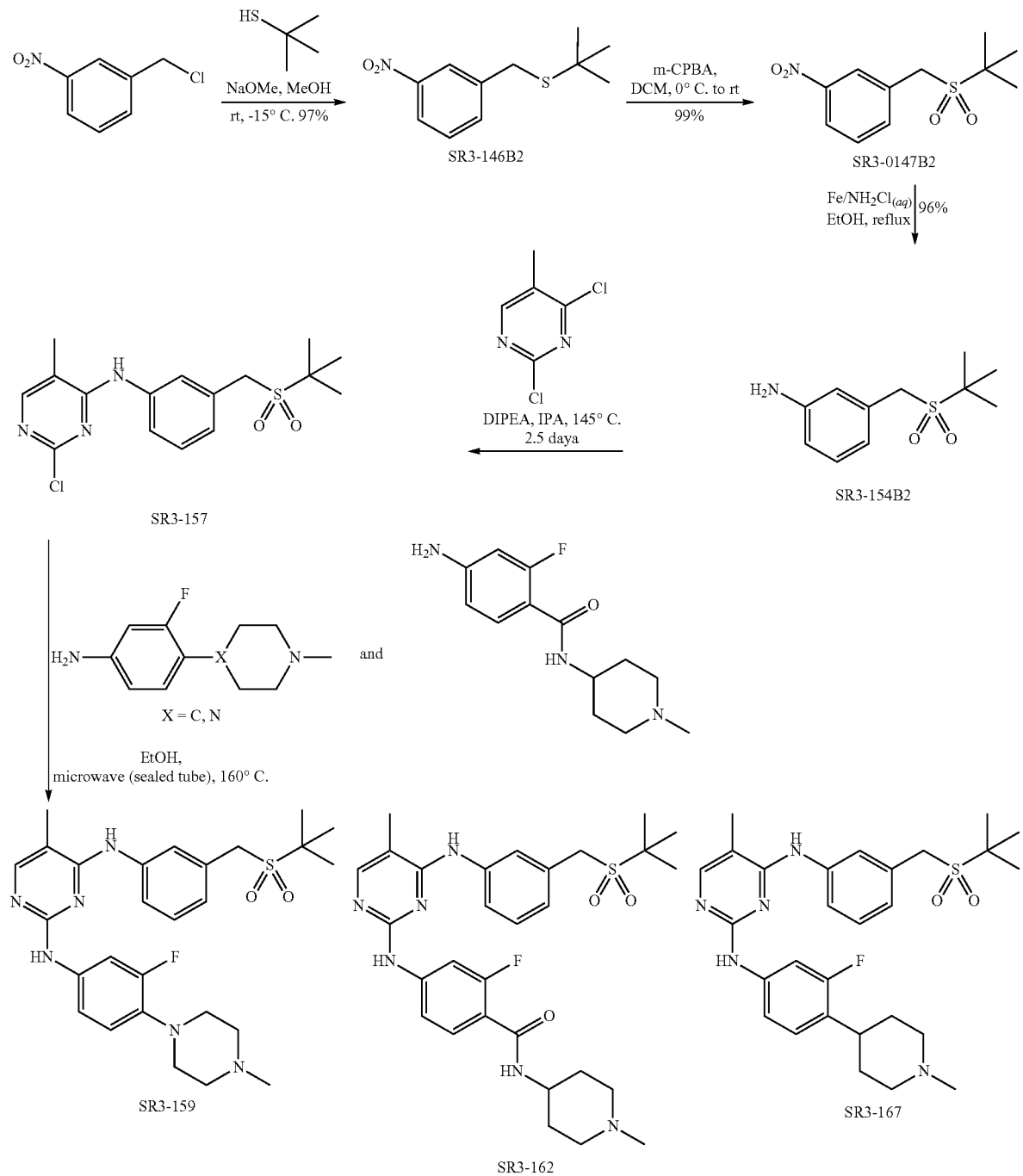

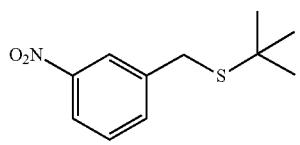

tert-Butyl (3-nitrobenzyl) sulfide (SR3-146). To sodium methoxide (1.574 g, 29.141 mmol) in dry MeOH (12 mL) under Ar was added 2-methyl-2-propanethiol (0.788 mL, 6.994 mmol) over 1 h. The mixture was cooled to −15° C. and 3-nitrobenzyl chloride (1.00 g, 5.828 mmol) was added in 3 portions. After stirring for 2 h at −15° C., the mixture was concentrated under reduced pressure and Et$_2$O (50 mL) added to the residue. The organic layer was washed with water (2×30 mL) and brine (1×30 mL), and dried (Na$_2$SO$_4$) and concentrated under reduce pressure to afford the sulfide as a yellow solid (1.206 g, 92%). $^1$H NMR (500 MHz, DMSO-d$_6$) δ 8.23 (m, 1H), 8.09 (ddd, J=8.2, 2.4, 1.0 Hz, 1H), 7.83 (ddd, J=7.6, 1.7, 1.0 Hz, 1H), 7.61 (t, J=7.9 Hz, 1H), 3.95 (s, 2H), 1.31 (s, 9H); $^{13}$C NMR (126 MHz, DMSO) δ 148.2, 142.3, 136.2, 130.3, 123.8, 122.1, 43.7, 32.1, 31.2. HPLC-MS (ESI+): m/z 226.2 [10% (M+H)+], 248.2 [100% (M+Na)+].

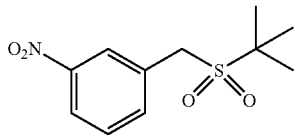 [SMILES: CC(C)(C)S(=O)(=O)Cc1cccc([N+](=O)[O-])c1]

tert-Butyl (3-nitrobenzyl) sulfone (SR3-147). The sulfide SR3-146 (1.184 g, 5.55 mmol) in dry dichloromethane (36 mL) under Ar at 0° C. was added m-CPBA (3.534 g, 15.765 mmol) and the mixture was allowed to warm to room temperature and stirred for 20 h. The reaction was quenched with 20% NaHSO$_3$ (1×40 mL) and extracted with DCM (2×50 mL). The combined organic layer was washed with sat. NaHCO$_3$ (2×30 mL), water (1×30 mL) and brine (1×40 mL) then dried (Na$_2$SO$_4$) and concentrated under reduce pressure to afford the sulfone SR3-147 as a white solid (1.35 g, 99%). $^1$H NMR (500 MHz, DMSO-d$_6$) δ 8.31 (t, J=1.9 Hz, 1H), 8.26 (ddd, J=8.2, 2.4, 1.1 Hz, 1H), 7.88-7.85 (m, 1H), 7.72 (t, J=7.9 Hz, 1H), 4.68 (s, 2H), 1.40 (s, 9H); $^{13}$C NMR (126 MHz, DMSO) δ 148.0, 138.7, 130.9, 130.2, 126.6, 123.6, 59.7, 50.6, 23.4. HPLC-MS (ESI+): m/z 280.1 [100% (M+Na)+], 537.2 [90% (2M+Na)+].

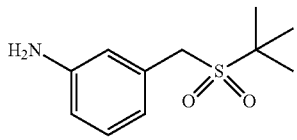

3-((tert-Butylsulfonyl)methyl)aniline (SR3-154). To the nitrobenzene derivative SR3-147 (1.500 g, 5.829 mmol) in EtOH (30 mL) was added iron (0.977 g, 17.489 mol) followed by aq. NH$_4$Cl (1.559 g, 29.148 mmol, 10 mL). The mixture was refluxed at 80° C. for 30 min and cooled to room temperature and filtered through Celite. The filtrate was diluted with EtOAc (50 mL) and washed with sat. NaHCO$_3$ (2×30 mL). The organic layer was dried (Na$_2$SO$_4$) and concentrated under reduce pressure to afford the aniline SR3-154 as a white solid (1.27 g, 96%). $^1$H NMR (500 MHz, DMSO-d$_6$) δ 7.00 (t, J=7.7 Hz, 1H), 6.59 (t, J=2.0 Hz, 1H), 6.54 (ddd, J=8.0, 2.3, 1.0 Hz, 1H), 6.51 (dt, J=7.6, 1.3 Hz, 1H), 5.12 (s, 2H), 4.21 (s, 2H), 1.35 (s, 9H); $^{13}$C NMR (126 MHz, DMSO) δ 149.0, 129.1, 128.7, 119.4, 117.3, 114.2, 59.3, 52.2, 23.5. HPLC-MS (ESI+): m/z 228.2 [80% (M+H)+], 455.3 [80% (2M+H)+].

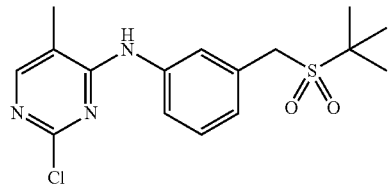 [SMILES: Cc1cnc(Cl)nc1Nc1cccc(CS(=O)(=O)C(C)(C)C)c1]

N-(3-((tert-Butylsulfonyl)methyl)phenyl)-2-chloro-5-methylpyrimidin-4-amine (SR3-157). 2,4-dichloro-5-methylpyrimidine (0.113 g, 0.966 mmol) and DIPEA (0.460 mL 2.639 mmol) were added to a solution of SR3-154 (0.200 g, 0.879 mmol) in dry isopropanol (4 mL) in a pressure vial. The mixture was heated at 145° C. in the sealed vial for 2.5 days, cooled and concentrated. The resulting residue was dissolved in EtOAc (25 mL) and washed with sat. NH$_4$Cl (1×20 mL), water (1×25 mL), and brine (1×20 mL). The organic layer was dried (Na$_2$SO$_4$) and concentrated under reduced pressure and purified by flash column chromatography using MeOH/DCM (0:100-10:90) as eluent to afford SR3-157 as an off-white solid (0.158 g, 50%). $^1$H NMR (500 MHz, DMSO-d$_6$) δ 8.96 (s, 1H), 8.06 (d, J=1.1 Hz, 1H), 7.72 (ddd, J=8.2, 2.2, 1.0 Hz, 1H), 7.58 (t, J=1.9 Hz, 1H), 7.39 (t, J=7.9 Hz, 1H), 7.16 (dt, J=7.7, 1.3 Hz, 1H), 4.42 (s, 2H), 2.19 (d, J=0.9 Hz, 3H), 1.38 (s, 9H); $^{13}$C NMR (126 MHz, DMSO) δ 160.8, 157.3, 156.8, 139.0, 128.9, 128.8, 127.7, 125.9, 122.8, 115.0, 59.5, 52.0, 25.9, 23.5, 14.4, 13.9. HPLC-MS (ESI+): m/z 354.1 [100% (M+H)+], 376.2 [40% (M+Na)+].

General Procedure a for the Synthesis of Analogs

To a mixture of N-(3-((tert-butylsulfonyl)methyl)phenyl)-2-chloro-5-methylpyrimidin-4-amine (SR3-157) (0.050 g, 0.141 mmol, 1 eq.) and aniline derivative (1 eq.) in EtOH (1.5 mL) was added aq. 6N HCl solution (1 eq.) and heated in a microwave reactor at 160° C. for 20 min. The mixture was cooled, concentrated and the resulting residue diluted with EtOAc (25 mL) and washed with sat. NaHCO$_3$ (1×20 mL). The aqueous layer was extracted with EtOAc (1×25 mL) and the combined organic layers were dried (Na$_2$SO$_4$) and concentrated under reduce pressure. Purification by flash column chromatography using MeOH/DCM (0:100-20:80) as eluent and trituration with DCM/hexane afforded the desired products.

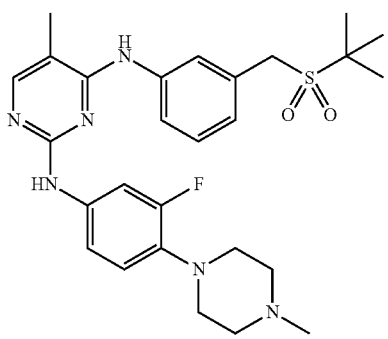 [SMILES: Cc1cnc(Nc2ccc(N3CCN(C)CC3)c(F)c2)nc1Nc1cccc(CS(=O)(=O)C(C)(C)C)c1]

N[4]-(3-((tert-Butylsulfonyl)methyl)phenyl)-N[2]-(3-fluoro-4-(4-methylpiperazin-1-yl)phenyl)-5-methylpyrimidine-2,4-diamine (SR3-159). SR3-159 was obtained as an off-white solid (0.028 g, 38%) from 3-fluoro-4-(4-methylpiperazin-1-yl)aniline (0.030 g, 0.141 mmol) using the general procedure A. HPLC: >97% [$t_R$=12.0 min, gradient 5-95% MeOH—H$_2$O (with 0.1% TFA), 20 min]. $^1$H NMR (500 MHz, DMSO-$d_6$) δ 8.96 (s, 1H), 8.42 (s, 1H), 7.91 (s, 1H), 7.81 (d, J=8.6 Hz, 1H), 7.66 (ddd, J=9.1, 7.1, 2.4 Hz, 2H), 7.34 (t, J=7.9 Hz, 1H), 7.25 (dd, J=8.5, 2.0 Hz, 1H), 7.10 (dt, J=7.6, 1.3 Hz, 1H), 6.88 (dd, J=10.1, 8.7 Hz, 1H), 4.38 (s, 2H), 2.92 (t, J=4.9 Hz, 4H), 2.45 (s, 4H), 2.22 (s, 3H), 2.12 (d, J=0.8 Hz, 3H), 1.36 (s, 9H); $^{19}$F NMR (471 MHz, DMSO-$d_6$) δ-122.40. HRMS (ESI+): m/z C$_{27}$H$_{36}$FN$_6$O$_2$S (M+H)$^+$527.2593; m/z C$_{27}$H$_{35}$FN$_6$O$_2$SNa (M+Na)$^+$ 549.1418; HPLC-MS (ESI+): m/z 527.3[40% (M+H)$^+$], (ESI-): m/z 525.3 [100%, (M-H)$^-$].

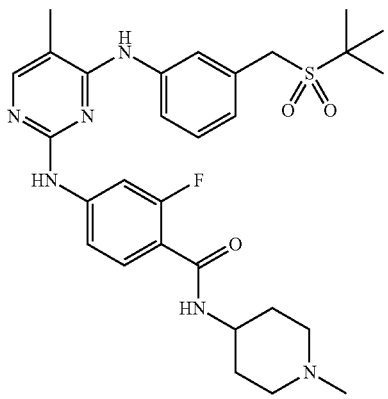 [SMILES: Cc1cnc(Nc2ccc(C(=O)NC3CCN(C)CC3)c(F)c2)nc1Nc1cccc(CS(=O)(=O)C(C)(C)C)c1]

4-((4-((3-((tert-Butylsulfonyl)methyl)phenyl)amino)-5-methylpyrimidin-2-yl)amino)-2-fluoro-N-(1-methylpiperidin-4-yl)benzamide (SR3-162). SR3-162 was obtained as an off-white solid (0.045 g, 56%) from 4-amino-2-fluoro-N-(1-methylpiperidin-4-yl)benzamide (0.026 g, 0.127 mmol) using the general procedure A. HPLC: >96% [$t_R$=14.6 min, gradient 5-95% MeOH—H$_2$O (with 0.1% TFA), 20 min]. $^1$H NMR (500 MHz, DMSO-$d_6$) δ 9.44 (s, 1H), 8.55 (s, 1H), 7.98 (d, J=1.0 Hz, 1H), 7.84-7.76 (m, 2H), 7.74 (dd, J=7.8, 3.5 Hz, 1H), 7.62 (t, J=1.9 Hz, 1H), 7.45 (t, J=8.6 Hz, 1H), 7.41-7.36 (m, 2H), 7.14 (dt, J=7.5, 1.3 Hz, 1H), 4.40 (s, 2H), 3.74-3.64 (m, 1H), 2.73 (d, J=11.3 Hz, 2H), 2.17 (s, 3H), 2.15 (s, 3H), 1.97 (m, 2H), 1.76 (m, 2H), 1.59-1.49 (m, 2H), 1.37 (s, 9H); $^{19}$F NMR (471 MHz, DMSO-$d_6$) δ-112.24-- 112.36 (m). HRMS (ESI+): m/z C$_{29}$H$_{38}$FN$_6$O$_3$S (M+H)$^+$ 569.2693; m/z C$_{29}$H$_{37}$FN$_6$O$_3$SNa (M+Na)$^+$591.2527; HPLC-MS (ESI+): m/z 569.2[40% (M+H)$^+$], (ESI-): m/z 567.3 [100%, (M-H)$^-$].

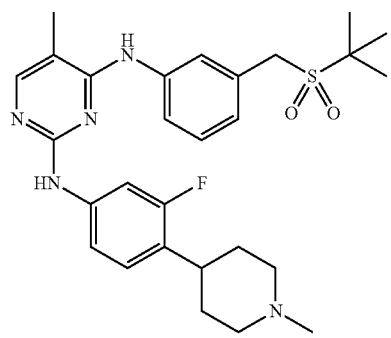 [SMILES: Cc1cnc(Nc2ccc(C3CCN(C)CC3)c(F)c2)nc1Nc1cccc(CS(=O)(=O)C(C)(C)C)c1]

N[4]-(3-((tert-Butylsulfonyl)methyl)phenyl)-N[2]-(3-fluoro-4-(1-methylpiperidin-4-yl)phenyl)-5-methylpyrimidine-2,4-diamine (SR3-167). SR3-167 was obtained as an off-white solid (0.042 g, 56%) from 3-fluoro-4-(1-methylpiperidin-4-yl)aniline (0.026 g, 0.127 mmol) using the general procedure A. HPLC: >98% [$t_R$=12.5 min, gradient 5-95% MeOH—H$_2$O (with 0.1% TFA), 20 min]. $^1$H NMR (500 MHz, DMSO-$d_6$) δ 9.09 (s, 1H), 8.46 (s, 1H), 7.93 (d, J=1.0 Hz, 1H), 7.81 (dt, J=8.2, 1.5 Hz, 1H), 7.71-7.63 (m, 2H), 7.35 (t, J=7.9 Hz, 1H), 7.29 (dd, J=8.5, 2.2 Hz, 1H), 7.15-7.06 (m, 2H), 4.39 (s, 2H), 2.85 (dd, J=11.3, 3.6 Hz, 2H), 2.67-2.58 (m, 1H), 2.19 (s, 3H), 2.13 (s, 3H), 1.95 (m, 2H), 1.74-1.58 (m, 4H), 1.36 (s, 9H); $^{13}$C NMR (126 MHz, DMSO) δ 159.6, 159.4, 158.3, 156.2, 141.2, 141.1, 140.2, 128.7, 128.4, 127.7, 127.7, 126.5, 125.4, 124.2, 124.1, 122.6, 114.6, 106.8, 105.4, 105.2, 59.4, 56.3, 51.9, 46.6, 34.6, 32.3, 31.4, 23.5, 22.5, 14.4, 14.0; $^{19}$F NMR (471 MHz, DMSO-$d_6$) δ-119.12 (m). HRMS (ESI+): m/z C$_{28}$H$_{37}$FN$_5$O$_2$S (M+H)$^+$526.2636; m/z C$_{28}$H$_{36}$FN$_5$O$_2$SNa (M+Na)$^+$548.2458; HPLC-MS (ESI+): m/z 526.3[40% (M+H)$^+$], (ESI-): m/z 524.3 [100%, (M-H)$^-$].

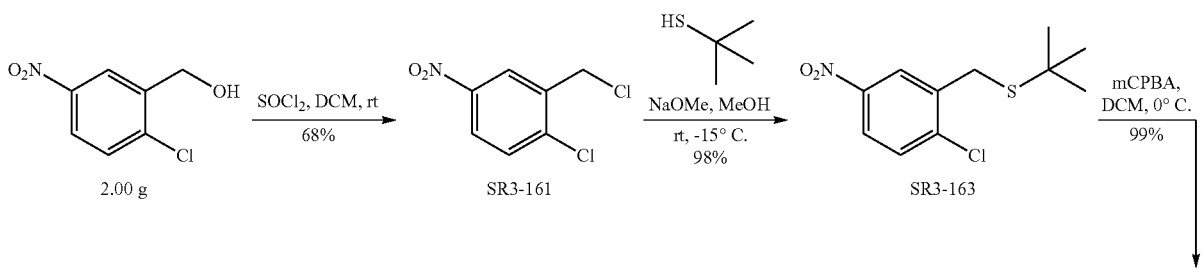

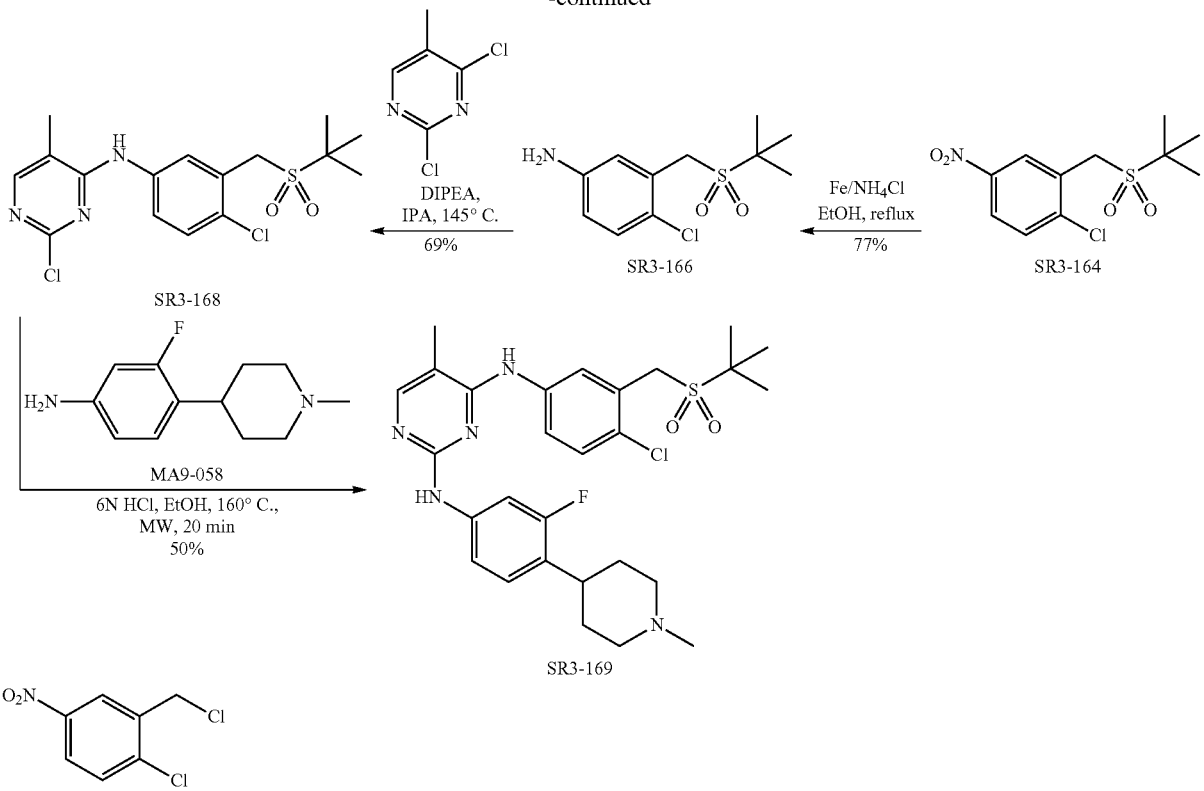

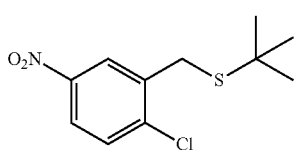 [SMILES: CC(C)(C)SCc1cc([N+](=O)[O-])ccc1Cl]

1-Chloro-2-(chloromethyl)-4-nitrobenzene (SR3-161). To 2-chloro-5-nitrobenzyl alcohol (2.00 g, 10.66 mmol) in dry DCM (25 mL) at room temperature, was added SOCl$_2$ (15.50 mL) dropwise. The mixture was stirred for 21 h and evaporated under reduced pressure. Purification by flash column chromatography using MeOH/DCM (0:100-20:80) as eluent afforded SR3-161 as a white solid (1.394 g, 68%). $^1$H NMR (500 MHz, DMSO-d$_6$) δ 8.57 (d, J=2.8 Hz, 1H), 8.24 (dd, J=8.8, 2.8 Hz, 1H), 7.84 (d, J=8.8 Hz, 1H), 4.97 (s, 2H); $^{13}$C NMR (126 MHz, DMSO) δ 146.92, 140.84, 137.43, 131.70, 126.62, 125.67, 43.10. HPLC-MS (ESI+): m/z 205.1[40% (M+H)$^+$], 227.1 [40%, (M+Na)$^+$].

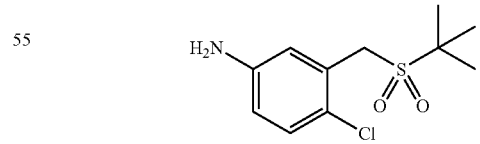

tert-butyl(2-chloro-5-nitrobenzyl)sulfane (SR3-163). The sulfide SR3-163 was obtained as a white solid (1.662 g, 98%) from 1-chloro-2-(chloromethyl)-4-nitrobenzene (1.338 g, 6.493 mmol) by the procedure used to make SR3-146. $^1$H NMR (500 MHz, DMSO-d$_6$) δ 8.41 (d, J=2.8 Hz, 1H), 8.12 (dd, J=8.8, 2.8 Hz, 1H), 7.75 (d, J=8.8 Hz, 1H), 4.01 (s, 2H), 1.34 (s, 9H); $^{13}$C NMR (126 MHz, DMSO) δ 146.8, 140.5, 139.3, 131.3, 126.3, 123.9, 43.9, 31.0, 30.3. HPLC-MS (ESI+): m/z 260.2[10% (M+H)$^+$], 282.2 [20% (M+Na)$^+$].

2-((tert-Butylsulfonyl)methyl)-1-chloro-4-nitrobenzene (SR3-164). The sulfone SR3-164 was obtained as an off-white solid (1.820 g, 99%) from tert-butyl(2-chloro-5-nitrobenzyl)sulfane (SR3-163)(1.628 g, 6.268 mmol) by the procedure used to make SR3-147. $^1$H NMR (500 MHz, DMSO-d$_6$) δ 8.40 (d, J=2.8 Hz, 1H), 8.26 (dd, J=8.8, 2.8 Hz, 1H), 7.86 (d, J=8.8 Hz, 1H), 4.80 (s, 2H), 1.44 (s, 9H); $^{13}$C NMR (126 MHz, DMSO) δ 146.4, 142.6, 131.5, 128.9, 128.6, 125.4, 60.1, 48.8, 23.2. MS (ESI+): m/z 314.1[80% (M+Na)$^+$], (ESI−): m/z 290.0 [100%, (M−H)$^−$].

3-((tert-Butylsulfonyl)methyl)-4-chloroaniline (SR3-166). The aniline SR3-166 was obtained as an off-white solid (0.433 g, 96%) from 2-((tert-butylsulfonyl)methyl)-1-chloro-4-nitrobenzene (SR3-164) (0.500 g, 1.714 mmol) by the procedure used to make SR3-154. $^1$H NMR (500 MHz, DMSO-d$_6$) δ 7.09 (d, J=8.6 Hz, 1H), 6.69 (d, J=2.8 Hz, 1H), 6.57 (dd, J=8.6, 2.8 Hz, 1H), 5.35 (s, 2H), 4.38 (s, 2H), 1.39

(s, 9H); $^{13}$C NMR (126 MHz, DMSO) δ 148.1, 130.0, 126.2, 121.0, 118.7, 115.9, 59.5, 49.2, 23.3. HPLC-MS (ESI+): m/z 262.2[60% (M+H)$^+$], 282.2 [70%, (2M+H)$^+$].

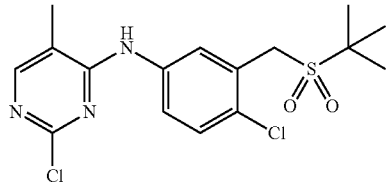 [SMILES: Cc1cnc(Cl)nc1Nc1ccc(Cl)c(CS(=O)(=O)C(C)(C)C)c1]

N-(3-((tert-Butylsulfonyl)methyl)-4-chlorophenyl)-2-chloro-5-methylpyrimidin-4-amine (SR3-168). The chloropyrimidine derivative SR3-168 was obtained as an off-white solid (0.205 g, 69%) from 3-((tert-butylsulfonyl)methyl)-4-chloroaniline (SR3-166) by the procedure used to make SR3-157. $^1$H NMR (500 MHz, DMSO-d$_6$) δ 9.08 (s, 1H), 8.10 (d, J=1.1 Hz, 1H), 7.81 (dd, J=8.8, 2.7 Hz, 1H), 7.73 (d, J=2.7 Hz, 1H), 7.53 (d, J=8.8 Hz, 1H), 4.56 (s, 2H), 2.19 (d, J=0.9 Hz, 3H), 1.43 (s, 9H); $^{13}$C NMR (126 MHz, DMSO) δ 160.6, 157.1, 138.1, 129.9, 129.9, 127.2, 126.7, 124.3, 115.3, 100.0, 59.8, 49.5, 23.3, 13.9. HRMS (ESI+): m/z C$_{16}$H$_{20}$C$_{12}$N$_3$O$_2$S (M+H)$^+$388.0642; m/z C$_{16}$H$_{19}$C$_{12}$N$_3$O$_2$SNa (M+Na)$^+$410.0473; HPLC-MS (ESI+): m/z 388.1[100% (M+H)$^+$], (ESI−): m/z 386.1 [100%, (M−H)$^−$].

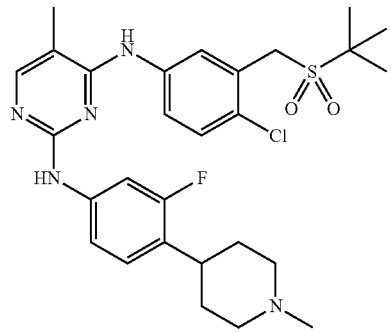 [SMILES: Cc1cnc(Nc2ccc(C3CCN(C)CC3)c(F)c2)nc1Nc1ccc(Cl)c(CS(=O)(=O)C(C)(C)C)c1]

N$^4$-(3-((tert-Butylsulfonyl)methyl)-4-chlorophenyl)-N$^2$-(3-fluoro-4-(1-methylpiperidin-4-yl)phenyl)-5-methylpyrimidine-2,4-diamine (SR3-169). The dianilinopyrimidine SR3-169 was obtained as an off-white solid (0.050 g, 70%) from 3-fluoro-4-(1-methylpiperidin-4-yl)aniline (0.024 g, 0.122 mmol) and the 2-chloropyrimidine SR3-168 (0.050 g, 0.128 mmol) using the general procedure A. HPLC: >96% [t$_R$=13.0 min, gradient 5-95% MeOH—H$_2$O (with 0.1% TFA), 20 min]. $^1$H NMR (500 MHz, DMSO-d$_6$) δ 9.10 (s, 1H), 8.61 (s, 1H), 7.96 (d, J=0.8 Hz, 1H), 7.88 (dd, J=8.8, 2.6 Hz, 1H), 7.79 (d, J=2.6 Hz, 1H), 7.67 (dd, J=14.0, 2.0 Hz, 1H), 7.45 (d, J=8.8 Hz, 1H), 7.27 (dd, J=8.5, 2.1 Hz, 1H), 7.12 (t, J=8.7 Hz, 1H), 4.53 (s, 2H), 2.85 (dd, J=11.7, 3.4 Hz, 2H), 2.72-2.57 (m, 1H), 2.19 (s, 3H), 2.13 (d, J=0.8 Hz, 3H), 1.95 (m, 2H), 1.76-1.59 (m, 4H), 1.41 (s, 9H); $^{13}$C NMR (126 MHz, DMSO) δ 161.3, 159.4, 158.1, 156.4, 141.1, 139.2, 129.6, 128.7, 126.9, 126.1, 124.3, 114.6, 107.0, 105.5, 105.2, 100.0, 59.7, 56.3, 49.3, 46.7, 34.6, 32.3, 31.4, 23.3, 22.5, 14.4, 14.0; $^{19}$F NMR (471 MHz, DMSO-d$_6$) δ-119.18 (dd, J=13.9, 8.8 Hz). HRMS (ESI+): m/z C$_{28}$H$_{36}$ClFN$_5$O$_2$S (M+H)$^+$560.2251; m/z C$_{28}$H$_{35}$ClFN$_5$O$_2$SNa (M+Na)+582.2064; HPLC-MS (ESI+): m/z 560.2[50% (M+H)$^+$], (ESI−): m/z 558.2 [100%, (M−H)$^−$].

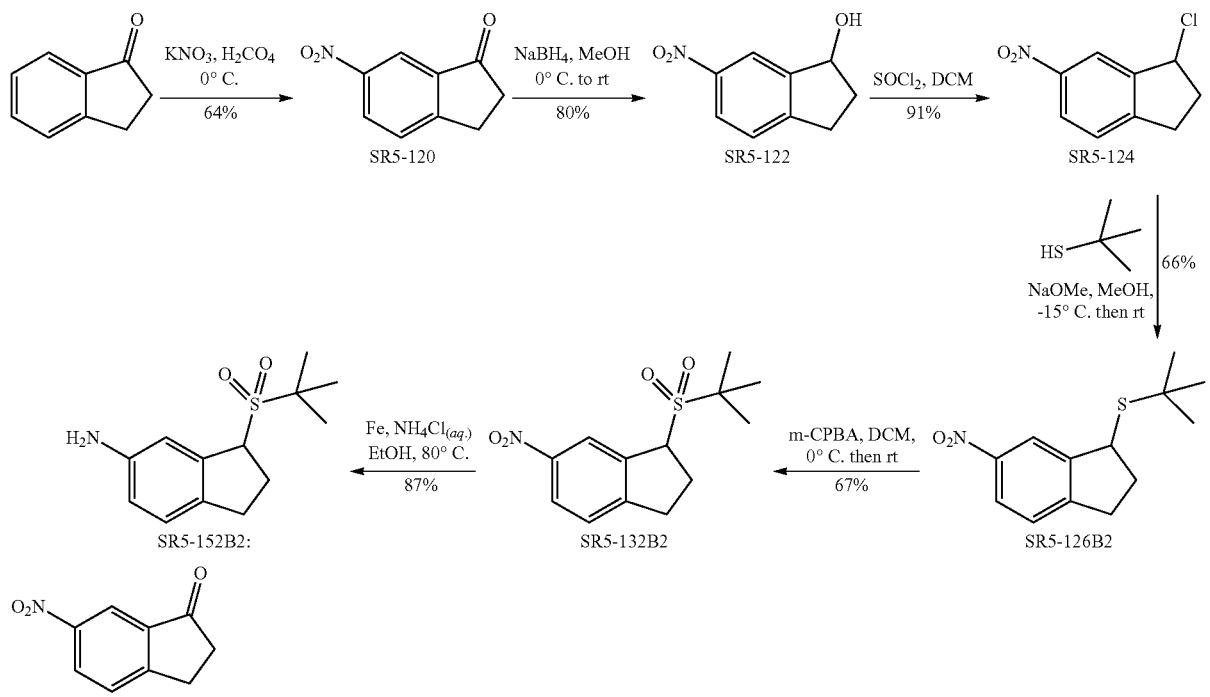

6-Nitro-2,3-dihydro-1H-inden-1-one (SR5-120). To 1-indanone (4.00 g, 30.266 mmol) in conc. $H_2SO_4$ (29 mL) at 0° C. was added solution of $KNO_3$ (3.060 g, 30.266 mmol) in conc. $H_2SO_4$ (9 mL) over 30 min. The mixture was stirred at 0° C. for 1 h and poured into ice/water mixture. The mixture was extracted with EtOAc (3×100 mL), dried ($Na_2SO_4$) and concentrated under reduced pressure. Purification by flash column chromatography using EtOAc/hexane (20:80-100:0) as eluent afforded SR5-120 as a pale yellow solid (3.410 g, 64%). $^1$H NMR (500 MHz, DMSO-$d_6$) δ 8.49 (dd, J=8.4, 2.3 Hz, 1H), 8.29 (dd, J=2.3, 0.7 Hz, 1H), 7.87 (dd, J=8.4, 0.8 Hz, 1H), 3.27-3.21 (m, 2H), 2.81-2.76 (m, 2H);

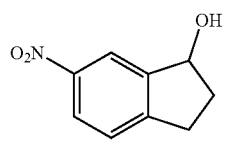 [SMILES: O=[N+]([O-])c1ccc2c(c1)C(O)CC2]

6-Nitro-indan-1-ol (SR5-122). To SR5-120 (3.30 g, 18.620 mmol) in dry MeOH (50 mL) at 0° C. was added $NaBH_4$ (0.705 g, 18.620 mmol) and stirred for 2 h. The mixture was concentrated under reduced pressure and the resulting residue dissolved in EtOAc (50 mL). The organic layer was washed with 1N HCl (25 mL), brine (25 mL), dried ($Na_2SO_4$) and concentrated under reduced pressure to afford SR5-122 as a white solid (2.662 g, 80%). $^1$H NMR (500 MHz, DMSO-$d_6$) δ 8.14 (d, J=2.3 Hz, 1H), 8.10 (ddd, J=8.2, 2.3, 0.5 Hz, 1H), 7.50 (d, J=8.1 Hz, 1H), 5.58 (d, J=5.5 Hz, 1H), 5.14 (m, J=6.5 Hz, 1H), 3.02 (ddd, J=17.0, 8.7, 3.6 Hz, 1H), 2.84 (dtd, J=17.7, 8.2, 1.1 Hz, 1H), 2.44 (dddd, J=12.8, 8.1, 7.1, 3.6 Hz, 1H), 1.86 (dtd, J=12.7, 8.5, 6.8 Hz, 1H). HPLC-MS (ESI+): m/z 180.2[10% (M+H)$^+$], 202.2 [100%, (M+Na)$^+$].

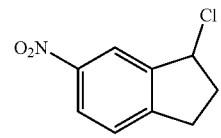 [SMILES: O=[N+]([O-])c1ccc2c(c1)C(Cl)CC2]

1-Chloro-6-nitroindane (SR5-124). To SR5-122 (2.410 g, 13.450 mmol) in dry DCM (40 mL) was added $SOCl_2$ (1.954 mL, 26.90 mmol) and the mixture stirred for 4 h at room temperature. The solvent was evaporated under reduced pressure to afford SR5-124 as a white solid (2.420 g, 91%). $^1$H NMR (500 MHz, DMSO-$d_6$) δ 8.24 (d, J=2.2 Hz, 1H), 8.18 (dd, J=8.3, 2.3 Hz, 1H), 7.60 (d, J=8.3 Hz, 1H), 5.73 (dd, J=6.6, 3.1 Hz, 1H), 3.19 (dtd, J=16.7, 7.7, 1.1 Hz, 1H), 3.03 (ddd, J=17.2, 8.1, 3.7 Hz, 1H), 2.69 (dtd, J=14.5, 7.8, 6.7 Hz, 1H), 2.34 (ddt, J=14.4, 7.8, 3.5 Hz, 1H). HPLC-MS (ESI+): m/z 198.0 [50% (M+H)$^+$], 220.1 [60%, (M+Na)$^+$].

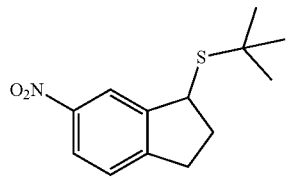 [SMILES: CC(C)(C)SC1CCc2ccc([N+](=O)[O-])cc21]

6-Nitroindan-1-yl (tert-butyl) sulfide (SR5-126)[1]. To sodium methoxide (3.308 g, 61.228 mmol) in dry MeOH (50 mL) under Ar was added 2-methyl-2-propanethiol (1.657 mL, 14.695 mmol) over 1 h. The mixture was cooled to 0° C. and 3-nitrobenzyl chloride (2.420 g, 12.246 mmol) added in 3 portions. After stirring for 20 h at room temperature, the mixture was concentrated under reduced pressure and $Et_2O$ (100 mL) added to the residue. The organic layer was washed with water (2×50 mL) followed by brine (40 mL), dried ($Na_2SO_4$) and concentrated under reduced pressure to afford the sulfide derivative SR5-126 as a yellow solid (2.021 g, 66%). $^1$H NMR (500 MHz, DMSO-$d_6$) δ 8.12-8.00 (m, 1H), 7.50 (d, J=8.2 Hz, 1H), 4.49 (t, J=7.4 Hz, 1H), 3.05 (ddd, J=17.0, 8.6, 4.5 Hz, 1H), 2.95 (dt, J=16.6, 7.9 Hz, 1H), 2.78-2.67 (m, 1H), 2.08 (ddt, J=12.9, 8.6, 7.6 Hz, 1H), 1.42 (s, 9H). HPLC-MS (ESI+): m/z 252.0 [10% (M+H)$^+$], 274.2 [100%, (M+Na)$^+$].

[1] prepared according to the procedure reported in WO 2012/143399 A1

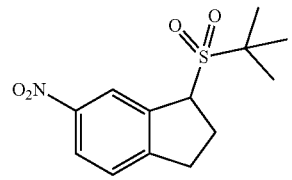 [SMILES: CC(C)(C)S(=O)(=O)C1CCc2ccc([N+](=O)[O-])cc21]

6-Nitroindan-1-yl (tert-butyl) sulfone (SR5-132). The sulfone SR5-132 was obtained as white solid (1.435 g, 67%) from the sulfide SR5-126 (1.912 g, 7.607 mmol) by the method used to make SR3-147. $^1$H NMR (500 MHz, DMSO-$d_6$) δ 8.25 (d, J=2.4 Hz, 1H), 8.20 (dd, J=8.4, 2.3 Hz, 1H), 7.60 (d, J=8.3 Hz, 1H), 5.27 (t, J=6.1 Hz, 1H), 3.18 (dt, J=16.8, 8.2 Hz, 1H), 3.05 (dt, J=17.4, 6.5 Hz, 1H), 2.66-2.58 (m, 2H), 1.44 (s, 9H); $^{13}$C NMR (126 MHz, DMSO) δ 154.4, 146.9, 137.8, 126.1, 124.5, 123.5, 61.9, 61.09, 32.1, 29.4, 23.8. HPLC-MS (ESI+): m/z 306.1 [70%, (M+Na)$^+$], 588.2 [100% (2M+Na)$^+$], (ESI−): m/z 561.3 [80%, (M−H)$^-$].

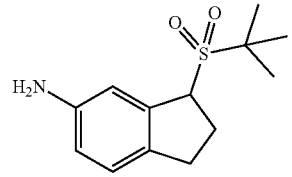

6-Aminoindan-1-yl (tert-butyl) sulfone (SR5-150). The amine SR5-150 was obtained as an off-white solid (0.383 g, 87%) from the nitrosulfone SR5-132 (0.500 g, 1.765 mmol) by the method used to make SR3-154. $^1$H NMR (500 MHz, DMSO-$d_6$) δ 6.93 (d, J=8.0 Hz, 1H), 6.73 (d, J=2.1 Hz, 1H), 6.52 (dd, J=8.0, 2.2 Hz, 1H), 4.97 (s, 2H), 4.89 (dd, J=8.4, 3.7 Hz, 1H), 2.90 (dt, J=15.6, 8.0 Hz, 1H), 2.70 (ddd, J=15.1, 8.7, 3.7 Hz, 1H), 2.49-2.36 (m, 2H), 1.39 (s, 9H); $^{13}$C NMR (126 MHz, DMSO) δ 147.5, 136.1, 132.7, 124.8, 115.4, 113.8, 63.0, 60.6, 30.9, 29.7, 24.0. HPLC-MS (ESI+): m/z 254.2 [100%, (M+H)$^+$], 507.3 [50% (2M+H)$^+$],

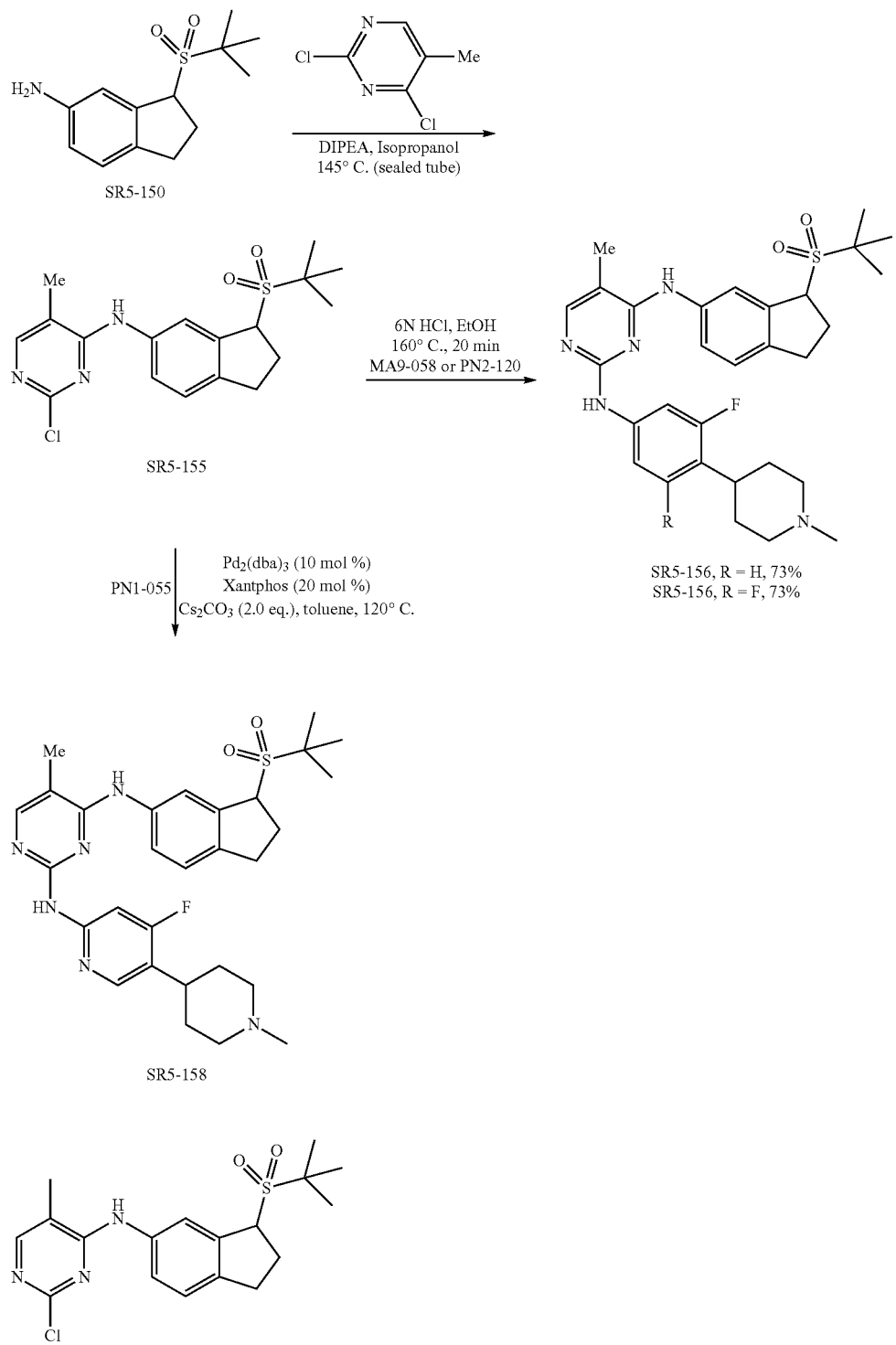

N-(3-(tert-Butylsulfonyl)-2,3-dihydro-1H-inden-5-yl)-2-chloro-5-methylpyrimidin-4-amine (SR5-155). The chloropyrimidine SR5-155 was obtained as a white solid (0.376 g, 83%) from the aminosulfone SR5-150 (0.302 g, 1.191 mmol) by the method used to make SR3-157. $^1$H NMR (500 MHz, DMSO-$d_6$) δ 8.92 (s, 1H), 8.03 (d, J=0.9 Hz, 1H), 7.68 (d, J=2.0 Hz, 1H), 7.60 (dd, J=8.2, 2.1 Hz, 1H), 7.30 (d, J=8.2 Hz, 1H), 5.11 (dd, J=8.3, 3.8 Hz, 1H), 3.07 (dt, J=16.2, 8.6 Hz, 1H), 2.89 (ddd, J=15.9, 8.6, 4.0 Hz, 1H), 2.61-2.53 (m, 2H), 2.18 (d, J=0.9 Hz, 3H), 1.42 (s, 9H); $^{13}$C NMR (126 MHz, DMSO) δ 161.0, 157.3, 156.7, 141.7, 137.2, 136.1, 124.6, 123.9, 122.7, 114.8, 62.8, 60.7, 55.4, 31.4, 29.6, 23.9, 14.0. HRMS (ESI+): m/z $C_{18}H_{23}ClN_3O_2S$ (M+H)+ 380.1196; m/z $C_{18}H_{22}ClN_3O_2SNa$ (M+Na)+ 402.1014; HPLC-MS (ESI+): m/z 380.2 [60% (M+H)+], (ESI−): m/z 378.0 [100%, (M−H)−].

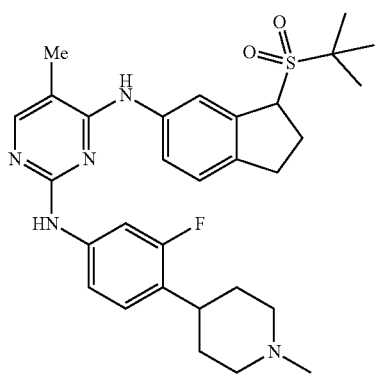 [SMILES: Cc1cnc(Nc2ccc(C3CCN(C)CC3)c(F)c2)nc1Nc1ccc2c(c1)C(S(=O)(=O)C(C)(C)C)CC2]

N[4]-(3-(tert-Butylsulfonyl)-2,3-dihydro-1H-inden-5-yl)-N[2]-(3-fluoro-4-(1-methylpiperidin-4-yl)phenyl)-5-methylpyrimidine-2,4-diamine (SR5-156). The diaminopyrimidine SR5-156 was obtained as an off-white solid (0.053 g, 73%) from 3-fluoro-4-(1-methylpiperidin-4-yl)aniline (0.026 g, 0.125 mmol) and the chloropyrimidine SR5-155 (0.050 g, 0.132 mmol) using the general procedure A. HPLC: >95% [$t_R$=8.8 min, 40% MeOH, 60% water (with 0.1% TFA), 20 min]. $^1$H NMR (500 MHz, DMSO-$d_6$) δ 9.06 (s, 1H), 8.44 (s, 1H), 7.90 (d, J=1.0 Hz, 1H), 7.71 (dd, J=8.2, 1.8 Hz, 1H), 7.68 (dd, J=14.1, 2.1 Hz, 1H), 7.65 (d, J=1.7 Hz, 1H), 7.32-7.24 (m, 2H), 7.07 (t, J=8.7 Hz, 1H), 5.00 (dd, J=8.1, 3.9 Hz, 1H), 3.09 (dt, J=16.1, 8.2 Hz, 1H), 2.91 (m, 3H), 2.71-2.54 (m, 3H), 2.27 (s, 3H), 2.12 (s, 3H), 2.11-2.00 (m, 2H), 1.81-1.59 (m, 4H), 1.38 (s, 9H); $^{19}$F NMR (471 MHz, DMSO-$d_6$) δ -119.1 (m). HRMS (ESI+): m/z $C_{30}H_{39}FN_5O_2S$ (M+H)$^+$552.2800; m/z $C_{30}H_{38}FN_5O_2SNa$ (M+Na)$^+$574.2623; HPLC-MS (ESI+): m/z 276.7 [100% (M+2H/2)$^+$], (ESI-): m/z 550.3 [40%, (M-H)$^-$].

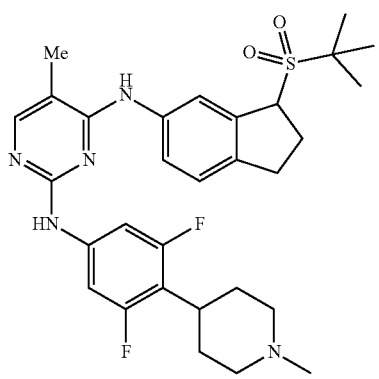 [SMILES: Cc1cnc(Nc2cc(F)c(C3CCN(C)CC3)c(F)c2)nc1Nc1ccc2c(c1)C(S(=O)(=O)C(C)(C)C)CC2]

N[4]-(3-(tert-Butylsulfonyl)-2,3-dihydro-1H-inden-5-yl)-N[2]-(3,5-difluoro-4-(1-methylpiperidin-4-yl)phenyl)-5-methylpyrimidine-2,4-diamine (SR5-157). The diaminopyrimidine SR5-157 was obtained as an off-white solid (0.024 g, 34%) from 3,5-difluoro-4-(1-methylpiperidin-4-yl)aniline (0.028 g, 0.125 mmol) and the chloropyrimidine SR5-155 (0.050 g, 0.132 mmol) using the general procedure A. HPLC: >97% [$t_R$=6.5 min, 40% MeOH, 60% water (with 0.1% TFA), 20 min]. $^1$H NMR (500 MHz, DMSO-$d_6$) δ 9.30 (s, 1H), 8.53 (s, 1H), 7.92 (d, J=1.0 Hz, 1H), 7.66 (dd, J=8.2, 2.1 Hz, 1H), 7.60 (d, J=1.9 Hz, 1H), 7.37 (d, J=12.0 Hz, 2H), 7.29 (d, J=8.2 Hz, 1H), 5.01 (dd, J=8.1, 3.9 Hz, 1H), 3.09 (dt, J=16.0, 8.1 Hz, 1H), 2.99-2.86 (m, 3H), 2.84-2.72 (m, 1H), 2.65-2.54 (m, 2H), 2.28 (s, 3H), 2.12 (s, 3H), 2.12-2.07 (m, 2H), 2.07-1.91 (m, 2H), 1.61 (s, 2H), 1.39 (s, 9H); $^{19}$F NMR (471 MHz, DMSO-$d_6$) δ -114.75 (d, J=11.6 Hz). HRMS (ESI+): m/z $C_{30}H_{38}F_2N_5O_2S$ (M+H)$^+$570.2705; m/z $C_{30}H_{37}F_2N_5O_2SNa$ (M+Na)+592.2525; HPLC-MS (ESI+): m/z 285.8 [100% (M+2H/2)$^+$], (ESI-): m/z 568.1 [40%, (M-H)$^-$].

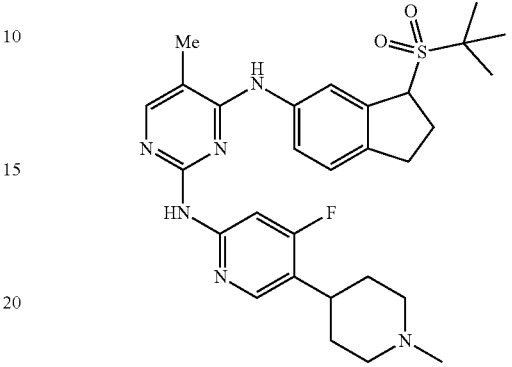

N[4]-(3-(tert-Butylsulfonyl)-2,3-dihydro-1H-inden-5-yl)-N[2]-(4-fluoro-5-(1-methylpiperidin-4-yl)pyridin-2-yl)-5-methylpyrimidine-2,4-diamine (SR5-158). The diaminopyrimidine SR5-155 (0.075 g, 0.197 mmol), 4-fluoro-5-(1-methylpiperidin-4-yl)pyridin-2-amine (0.036 g, 0.177 mmol), $Cs_2CO_3$ (0.128 g, 0.394 mmol), and Xantphos (0.023 g, 0.0394 mmol) were dissolved in dry toluene (1.75 mL) in a pressure vial and degassed with Ar for 10 min. To the mixture, $Pd_2(dba)_3$ (0.018 g, 0.0197 mmol) was added and the sealed vial placed in an oil bath at 120° C. for 20 h. The reaction mixture was diluted with EtOAc and the organic layer washed with sat. $NaHCO_3$ (25 mL). The aqueous layer was extracted with EtOAc (25 mL) and the combined organic layer dried ($Na_2SO_4$) and concentrated under reduced pressure. Purification by flash column chromatography using MeOH/DCM (0:100-20:80) as eluent afforded SR5-158 as a white solid (isolated 0.019 g 25% along with 0.023 g as a mixture). HPLC: >99% [$t_R$=10.6 min, 40% MeOH, 60% water (with 0.1% TFA), 20 min]. $^1$H NMR (500 MHz, DMSO-$d_6$) δ 9.19 (d, J=1.6 Hz, 1H), 8.56 (s, 1H), 8.13 (d, J=11.0 Hz, 1H), 7.95 (d, J=14.0 Hz, 2H), 7.73 (dd, J=8.1, 1.9 Hz, 1H), 7.69 (d, J=1.6 Hz, 1H), 7.27 (d, J=8.2 Hz, 1H), 5.02 (dd, J=8.1, 3.9 Hz, 1H), 3.09 (dt, J=16.1, 8.1 Hz, 1H), 2.94-2.76 (m, 3H), 2.66-2.54 (m, 2H), 2.19 (s, 3H), 2.14 (s, 3H), 1.95 (m, 2H), 1.83-1.63 (m, 4H), 1.39 (s, 9H); $^{13}$C NMR (126 MHz, DMSO) δ 168.4, 166.4, 159.8, 157.1, 155.9, 154.3, 148.5, 148.4, 140.8, 138.1, 135.7, 124.6, 124.1, 122.8, 121.5, 107.7, 107.7, 99.1, 98.9, 62.7, 60.7, 56.2, 46.6, 33.8, 31.9, 31.4, 29.7, 23.9, 14.1; $^{19}$F NMR (471 MHz, DMSO-$d_6$) δ -108.90. HRMS (ESI+): m/z $C_{29}H_{38}FN_6O_2S$ (M+H)$^+$553.2754; m/z $C_{29}H_{37}FN_6O_2SNa$ (M+Na)$^+$575.2570; HPLC-MS (ESI+): m/z 277.3 [100% (M+2H/2)$^+$], (ESI-): m/z 551.3 [30%, (M-H)$^-$].

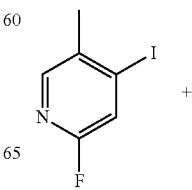

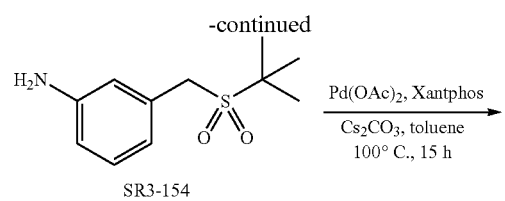

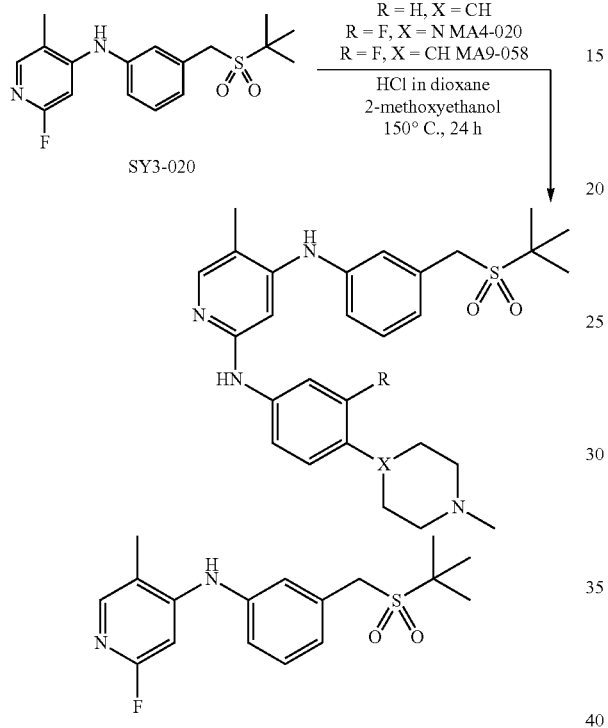

N-(3-((tert-Butylsulfonyl)methyl)phenyl)-2-fluoro-5-methylpyridin-4-amine (SY3-020). This compound was synthesized by the same procedure described for SY3-014 using SR3-154 (0.227 g, 0.1 mmol) to afford an off-white solid (0.25 g, 75%). $^1$H NMR (500 MHz, DMSO-d$_6$) δ 8.20 (s, 1H), 7.76 (s, 1H), 7.41 (t, J=8.0 Hz, 1H), 7.39 (s, 1H), 7.27 (d, J=8.0 Hz, 1H), 7.16 (d, J=8.0 Hz, 1H), 6.44 (s, 1H), 4.44 (s, 2H), 2.18 (s, 3H).6.90 (t, J=9 Hz, 1H), 6.47 (s, 1H), 2.92 (br s, 4H), 2.47 (br s, 4H), 2.29 (s, 3H), 2.10 (s, 3H), 1.37 (s, 9H). HPLC-MS (ESI+): m/z 337.2 (M+1)$^+$.

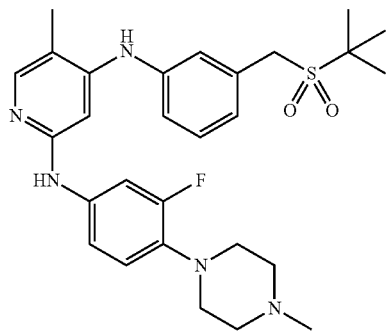 [SMILES: Cc1cnc(Nc2ccc(N3CCN(C)CC3)c(F)c2)cc1Nc1cccc(CS(=O)(=O)C(C)(C)C)c1]

N$^4$-(3-((tert-Butylsulfonyl)methyl)phenyl)-N$^2$-(3-fluoro-4-(4-methylpiperazin-1-yl)phenyl)-5-ethylpyridine-2,4-diamine (SY3-026). This compound was synthesized by the same procedure described for SY3-005 using SY3-020 (0.05 g, 0.149 mmol) and MA4-020 (0.031 g, 0.149 mmol) to afford an off-white solid (0.033 g, 43%). $^1$H NMR (500 MHz, DMSO-d$_6$) δ 8.54 (s, 1H), 7.77 (s, 1H), 7.71 (s, 1H), 7.68 (dd, J=15.5, 2.5 Hz, 1H), 7.37 (t, J=7.5 Hz, 1H), 7.25 (d, J=7.5 Hz, 1H), 7.23 (s, 1H), 7.09-7.05 (m, 2H), 6.90 (dd, J=10.1, 8.8 Hz, 1H), 6.42 (s, 1H), 4.43 (s, 2H), 2.89 (br s, 4H), 2.45 (br s, 4H), 2.21 (s, 3H), 2.11 (s, 3H), 1.38 (s, 9H). $^{13}$C NMR (125 MHz, DMSO-d$_6$) δ 155.9 (d, J=240 Hz), 155.2, 150.1, 149.5, 141.3, 138.2 (d, J=11.3 Hz), 132.1 (d, J=9.5 Hz), 129.0 (d, J=22.3 Hz), 125.7, 124.6, 121.1, 119.4 (d, J=4.2 Hz), 113.2, 112.3, 105.6 (d, J=25.8 Hz), 58.9, 54.8, 51.2, 50.6, 45.8, 23.0, 14.2. $^{19}$F NMR (471 MHz, DMSO-d$_6$) δ-122.47 (dd, J=15.8, 10.0 Hz). HPLC-MS (ESI+): m/z 526.3 (M+1)$^+$. HRMS (ESI+): m/z calcd for C$_{28}$H$_{37}$FN$_5$O$_2$S (M+H)$^+$526.2647, found 527.2638.

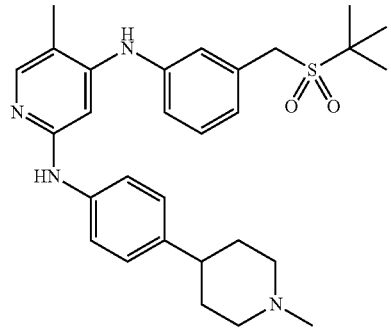

N$^4$-(3-((tert-Butylsulfonyl)methyl)phenyl)-5-methyl-N$^2$-(4-(1-methylpiperidin-4-yl)phenyl)pyridine-2,4-diamine (SY3-032). This compound was synthesized by the same procedure described for SY3-005 except using SY3-020 (0.05 g, 0.149 mmol) and 4-(1-methylpiperidin-4-yl)aniline (0.028 g, 0.149 mmol) to afford an off-white solid (0.028 g, 37%). HPLC: 99% [t$_R$=10.93 min, 5-95% gradient elution MeOH/water (with 0.1% TFA), 20 min, 254 nm]. $^1$H NMR (500 MHz, DMSO-d$_6$) δ 8.41 (s, 1H), 7.75 (s, 1H), 7.69 (s, 1H), 7.46 (d, J=8.5 Hz, 2H), 7.35 (t, J=8.5 Hz, 1H), 7.24-7.23 (m, 2H), 7.05-7.03 (m, 3H), 6.47 (s, 1H), 4.39 (s, 2H), 2.85 (d, J=12 Hz, 2H), 2.33 (tt, J=12, 4 Hz, 1H), 2.18 (s, 3H), 2.11 (s, 3H), 1.94 (t, J=11 Hz, 2H), 1.69-1.56 (m, 4H), 1.37 (s, 9H). $^{13}$C NMR (125 MHz, DMSO-d$_6$) δ 155.5, 150.0, 147.1, 141.5, 140.4, 137.3, 128.9, 128.8, 126.5, 125.5, 124.4, 120.8, 117.7, 112.1, 93.1, 58.9, 55.9, 51.3, 46.1, 40.5, 33.2, 23.0, 14.2. HPLC-MS (ESI+): m/z 507.3 (M+1)$^+$. HRMS (ESI+): m/z calcd for C$_{29}$H$_{39}$N$_4$O$_2$S (M+H)$^+$507.2788, found 508.2783.

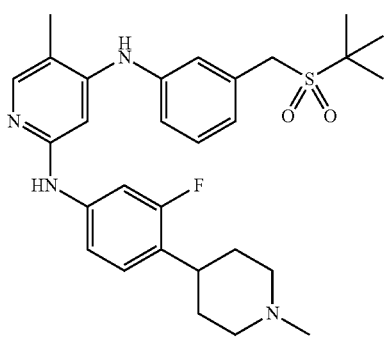 [SMILES: Cc1cnc(Nc2ccc(C3CCN(C)CC3)c(F)c2)cc1Nc1cccc(CS(=O)(=O)C(C)(C)C)c1]

N[4]-(3-((tert-Butylsulfonyl)methyl)phenyl)-N[2]-(3-fluoro-4-(1-methylpiperidin-4-yl)phenyl)-5-methylpyridine-2,4-diamine (SY3-036). This compound was synthesized by the same procedure described for SY3-005 using SY3-020 (0.05 g, 0.149 mmol) and MA9-058 (0.031 g, 0.149 mmol) to afford a yellow solid (0.032 g, 41%). HPLC: 98% [$t_R$=11.07 min, 5-95% gradient elution MeOH/water (with 0.1% TFA), 20 min, 254 nm]. $^1$H NMR (500 MHz, DMSO-$d_6$) δ 8.68 (s, 1H), 8.79 (s, 1H), 7.73 (s, 1H), 7.69 (dd, J=14, 2 Hz, 1H), 7.36 (t, J=8 Hz, 1H), 7.26-7.23 (m, 2H), 7.11-7.06 (m, 3H), 6.46 (s, 1H), 4.40 (s, 2H), 2.86 (d, J=11.5, 2H), 2.60 (m, 1H), 2.18 (s, 3H), 2.12 (s, 1H), 1.95 (m, 2H), 1.67-1.63 (m, 4H), 1.37 (s, 9H), $^{13}$C NMR (125 MHz, DMSO-$d_6$) δ 160.9 (d, J=238 Hz), 155.1, 150.7, 150.3, 147.6, 142.1 (d, J=11.6 Hz), 141.3, 129.0 (d, J=23.8 Hz), 127.3 (d, J=6.8 Hz), 125.8, 124.8, 122.6 (d, J=15.3 Hz), 121.2, 113.2, 112.6, 103.9 (d, J=27.8 Hz), 93.4, 58.9, 55.8, 51.2, 46.2, 34.0, 31.8, 23.0, 14.2. $^{19}$F NMR (471 MHz, DMSO-$d_6$) δ-119.2 (dd, J=14.1, 9.4 Hz). HPLC-MS (ESI+): m/z 525.3 (M+1)$^+$. HRMS (ESI+): m/z calcd for $C_{29}H_{38}FN_5O_2S$ (M+H)$^+$525.2694, found 525.2.

Table 3 below shows inhibitory activity of compounds disclosed herein.

TABLE 3

| ID | BRD4 DSF (ΔTm) °C. | BRD4 (IC50) μM | JAK2 (IC50) μM | GI50 (UKE1) μM | GI50 (MM1S) μM |
|---|---|---|---|---|---|
| SR3-159 | 8.4 | 5.6 | 0.008 | 0.44 | 0.71 |
| SR3-162 | 6.9 | | 0.0022 | | 0.13 |
| SR3-167 | 9.2 | 0.7 | 0.001 | 0.21 | 0.14 |
| SR3-169 | 9.8 | 0.7 | 0.0042 | 0.40 | 0.32 |
| SR5-156 | 8.7 | | | 1.44 | 0.85 |
| SR5-157 | | | | 1.50 | 0.7 |
| SR5-158 | 7.0 | | | 3.64 | 2.3 |
| SY3-026 | 2.3 | 10 | 1 | | |
| SY3-032 | 2.5 | | | | |
| SY3-036 | 2.9 | | | | |

REFERENCES

1. Lawrence, H. R.; Mahajan, K.; Luo, Y.; Zhang, D.; Tindall, N.; Huseyin, M.; Gevariya, H.; Kazi, S.; Ozcan, S.; Mahajan, N. P.; Lawrence, N. J. Development of novel ACK1/TNK2 inhibitors using a fragment-based approach. *J Med Chem* 2015, 58, 2746-63.
2. Lawrence, H. R.; Martin, M. P.; Luo, Y.; Pireddu, R.; Yang, H.; Gevariya, H.; Ozcan, S.; Zhu, J. Y.; Kendig, R.; Rodriguez, M.; Elias, R.; Cheng, J. Q.; Sebti, S. M.; Schonbrunn, E.; Lawrence, N. J. Development of o-chlorophenyl substituted pyrimidines as exceptionally potent aurora kinase inhibitors. *J. Med. Chem.* 2012, 55, 7392-416.
3. Richter, D. T.; Kath, J. C.; Luzzio, M. J.; Keene, N.; Berliner, M. A.; Wessel, M. D. Selective addition of amines to 5-trifluoromethyl-2,4-dichloropyrimidine induced by Lewis acids. *Tetrahedron Letters* 2013, 54, 4610-4612.
4. McIver, E. G.; Bryans, J.; Birchall, K.; Chugh, J.; Drake, T.; Lewis, S. J.; Osborne, J.; Smiljanic-Hurley, E.; Tsang, W.; Kamal, A.; Levy, A.; Newman, M.; Taylor, D.; Arthur, J. S.; Clark, K.; Cohen, P. Synthesis and structure-activity relationships of a novel series of pyrimidines as potent inhibitors of TBK1/IKKepsilon kinases. *Bioorg Med Chem Lett* 2012, 22, 7169-73.
5. Zhang, Z.; Wallace, M. B.; Feng, J.; Stafford, J. A.; Skene, R. J.; Shi, L.; Lee, B.; Aertgeerts, K.; Jennings, A.; Xu, R.; Kassel, D. B.; Kaldor, S. W.; Navre, M.; Webb, D. R.; Gwaltney, S. L. Design and synthesis of pyrimidinone and pyrimidinedione inhibitors of dipeptidyl peptidase IV. *J Med Chem* 2011, 54, 510-24.
6. Kath, J.; Luzzio, M. Pyrimidine derivatives for the treatment of abnormal cell growth. US Pat. Appl. US2005/0256125A1, 2005.
7. Moore, M.; Moorhouse, A. D.; Moses, J. E.; Neidle, S. Ureylene derivatives. WO2008/122667A3, 2008.
8. Ueda, S.; Nagasawa, H. Copper-catalyzed synthesis of benzoxazoles via a regioselective C—H functionalization/C—O bond formation under an air atmosphere. *J Org Chem* 2009, 74, 4272-7.
9. Radi, M.; Botta, M.; Falchi, F.; Maga, G.; Baldanti, F.; Paolucci, S. Compounds with ddx3 inhibitory activity and uses thereof. WO2011/039735A3, 2011.
10. Brooks, C. A.; Cheung, M.; Eidam, H. S.; Fox, R. M.; Hilfker, M. A.; Manas, E. S.; Ye, G. Antagonistes de trpv4. WO2011/119704A1, 2011.
11. Lawrence, H. R.; Kazi, A.; Luo, Y.; Kendig, R.; Ge, Y.; Jain, S.; Daniel, K.; Santiago, D.; Guida, W. C.; Sebti, S. M. Synthesis and biological evaluation of naphthoquinone analogs as a novel class of proteasome inhibitors. *Bioorg Med Chem* 2010, 18, 5576-92.
12. Altenbach, R. J.; Khilevich, A.; Kolasa, T.; Rohde, J. J.; Bhatia, P. A.; Patel, M. V.; Searle, X. B.; Yang, F.; Bunnelle, W. H.; Tietje, K.; Bayburt, E. K.; Carroll, W. A.; Meyer, M. D.; Henry, R.; Buckner, S. A.; Kuk, J.; Daza, A. V.; Milicic, I. V.; Cain, J. C.; Kang, C. H.; Ireland, L. M.; Carr, T. L.; Miller, T. R.; Hancock, A. A.; Nakane, M.; Esbenshade, T. A.; Brune, M. E.; O'Neill, A. B.; Gauvin, D. M.; Katwala, S. P.; Holladay, M. W.; Brioni, J. D.; Sullivan, J. P. Synthesis and structure-activity studies on N-[5-(1H-imidazol-4-yl)-5,6,7,8-tetrahydro-1-naphthalenyl]methanesulfonamide, an imidazole-containing alpha (1A)-adrenoceptor agonist. *J Med Chem* 2004, 47, 3220-35.
13. Sun, P.; Weinreb, S. M.; Shang, M. tert-Butylsulfonyl (Bus), a New Protecting Group for Amines. *J Org Chem* 1997, 62, 8604-8608.
14. Gunawan, S., Hulme, C. Construction of functionalized tricyclic dihydropyrazino-quinazolinedione chemotypes via an Ugi/N-acyliminium ion cyclization cascade. *Tet. Lett.* 2013, 54, 4467-4470.
15. Tangallapally, R. P.; Yendapally, R.; Lee, R. E.; Lenaerts, A. J. Synthesis and evaluation of cyclic secondary amine substituted phenyl and benzyl nitrofuranyl amides as novel antituberculosis agents. *J Med Chem* 2005, 48, 8261-9.
16. Casillas, L. N.; Chakravorty, S. J.; Eidam, P.; Haile, P. A.; Hughes, T. V.; Lakdawala, S. A.; Leister, L. K.; Miller, N. A.; Rahman, A.; Sehon, C. A. Pyrazolyl-pyrimidines as kinase inhibitors. WO2011/120026A1, 2011.

17. Hollick, J. J.; Jones, S. D.; Flynn, C. J.; Thomas, M. G. Pyrimidine derivatives as protein kinase inhibitors. U.S. Pat. No. 8,563,542B2, 2013.
What is claimed is:
1. A compound selected from:
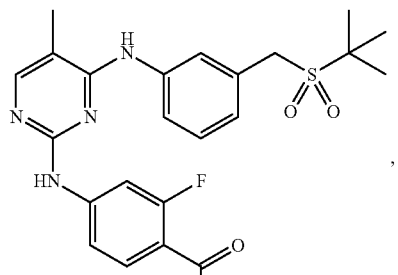
,
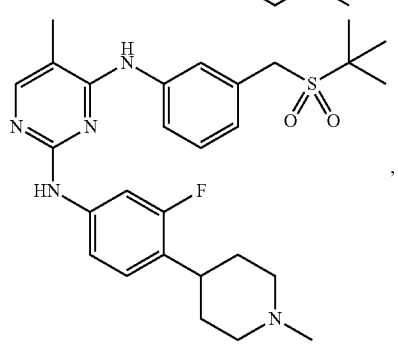
,
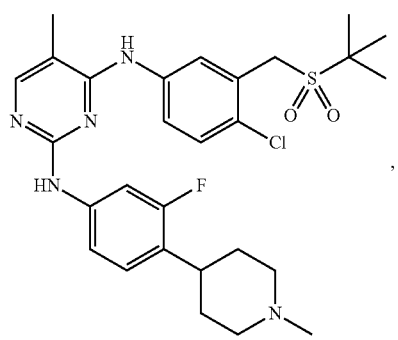
,
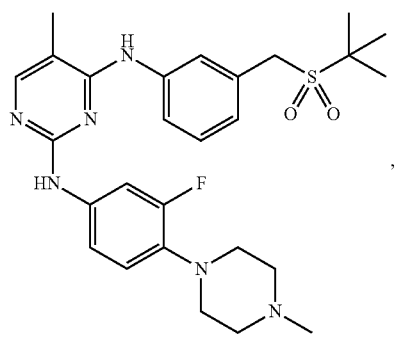
,
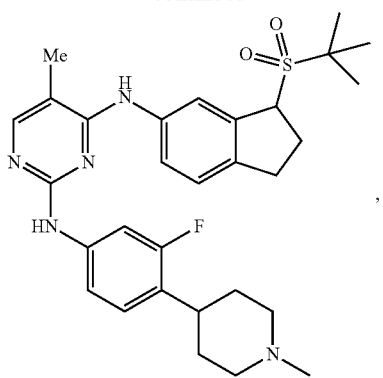
,
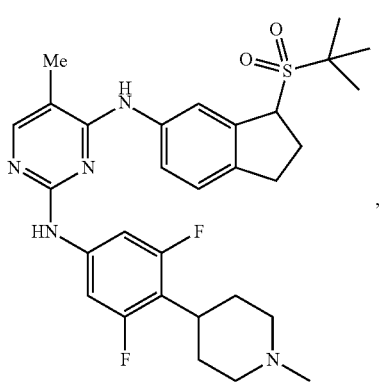
,
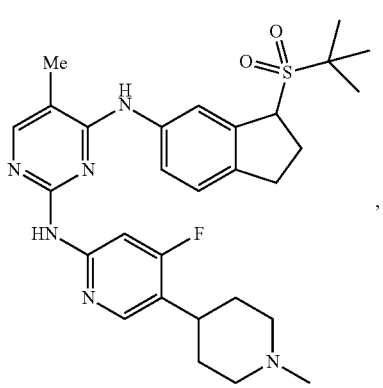
,
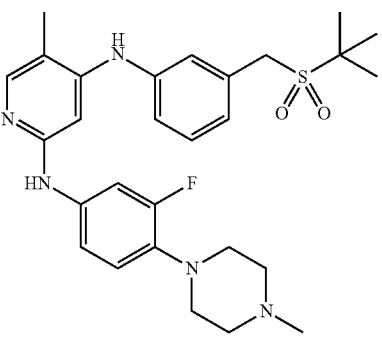
, -continued

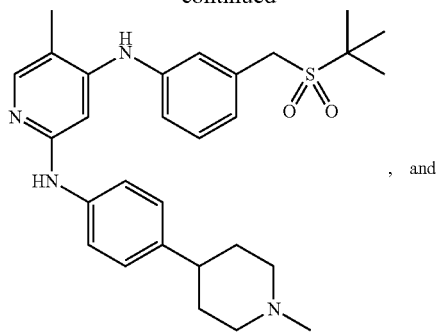

or a salt thereof.

2. A pharmaceutical composition comprising a compound of claim 1 and a pharmaceutically acceptable carrier.

3. A method of ameliorating or alleviating cancer in a subject comprising administering to the subject an effective amount of a compound of claim 1.

4. A method of killing a tumor cell in a subject comprising: contacting the tumor cell with an effective amount of a compound of claim 1.

5. A compound selected from:

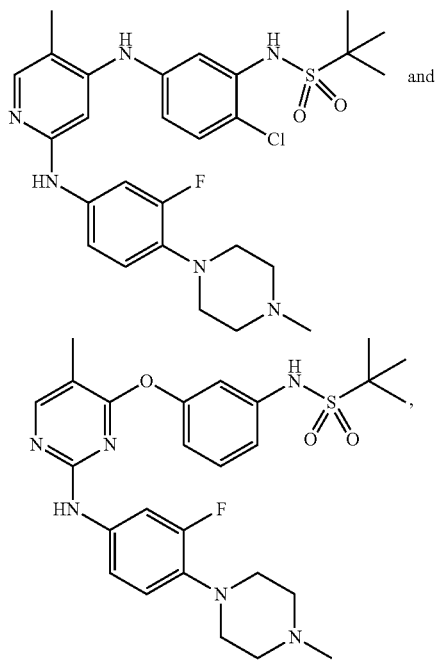

or a salt thereof.

6. A pharmaceutical composition comprising a compound of claim 5 and a pharmaceutically acceptable carrier.

7. A method of ameliorating or alleviating cancer in a subject comprising administering to the subject an effective amount of a compound of claim 5.

8. A method of killing a tumor cell in a subject comprising: contacting the tumor cell with an effective amount of a compound of claim 5.

* * * * *